US010646405B2

(12) United States Patent
Ranalletta et al.

(10) Patent No.: US 10,646,405 B2
(45) Date of Patent: May 12, 2020

(54) WORK STATION FOR MEDICAL DOSE PREPARATION SYSTEM

(71) Applicant: BAXTER CORPORATION ENGLEWOOD, Englewood, CO (US)

(72) Inventors: Joseph V. Ranalletta, Englewood, CO (US); Wesley J. Weber, Golden, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 0 days.

(21) Appl. No.: 16/027,805

(22) Filed: Jul. 5, 2018

(65) Prior Publication Data

US 2018/0311107 A1    Nov. 1, 2018

Related U.S. Application Data

(63) Continuation of application No. 15/193,494, filed on Jun. 27, 2016, now Pat. No. 10,045,912, which is a (Continued)

(51) Int. Cl.
*A61J 3/00* (2006.01)
*G06Q 10/06* (2012.01)
(Continued)

(52) U.S. Cl.
CPC .............. *A61J 3/00* (2013.01); *A47B 13/003* (2013.01); *A47B 13/10* (2013.01); *A47B 37/00* (2013.01);
(Continued)

(58) Field of Classification Search
CPC ........ A61J 3/00; A61J 7/0076; A61J 2200/74; G06F 19/3462; G16H 20/10; G16H 20/13;
(Continued)

(56) References Cited

U.S. PATENT DOCUMENTS

| 641,748 A | 1/1900 | Smith |
| 819,339 A | 5/1906 | Cleland |
| (Continued) | | |

FOREIGN PATENT DOCUMENTS

| CN | 1516257 | 5/1999 |
| CN | 2440518 | 8/2001 |
| (Continued) | | |

OTHER PUBLICATIONS

GE ImageQuant TL 7.0 Image Analysis Sollware User Manual, May 2007, http://nba.uth.tmc.edu/Assets/pdf/other/yphoon_supporting_files/IQTL_UserManual.pdf, Uppsala, Sweden.
(Continued)

*Primary Examiner* — Allen C Wong
(74) *Attorney, Agent, or Firm* — K&L Gates LLP

(57) ABSTRACT

Embodiments of work stations for use in medical dose preparation management system. A work station may include a camera stand. The camera stand may include a housing enclosing a camera and one or more light sources therein. As such, the camera and light sources may be directed at a medical dose preparation staging region to capture medical dose preparation images of the medical dose preparation staging region. The camera stand may include an adjustable support positionable in a plurality of positions to dispose the camera and light source relative to the medical dose preparation staging region. A base with a removable tray may be provided that include medical receptacle engagement features. The work stations may facilitate improved image quality, efficiency of work flows carried out at the work station, and administrative tasks such as cleaning.

17 Claims, 15 Drawing Sheets

Related U.S. Application Data continuation of application No. 14/438,559, filed as application No. PCT/US2013/032545 on Mar. 15, 2013, now Pat. No. 9,375,079.

(60) Provisional application No. 61/719,256, filed on Oct. 26, 2012.

(51) Int. Cl.
| | |
|---|---|
| *G06K 9/20* | (2006.01) |
| *G16H 40/63* | (2018.01) |
| *A47B 37/00* | (2006.01) |
| *F21V 9/14* | (2006.01) |
| *H04N 7/18* | (2006.01) |
| *A47B 13/00* | (2006.01) |
| *A47B 13/10* | (2006.01) |
| *G01G 19/414* | (2006.01) |
| *A61J 7/00* | (2006.01) |
| *H04N 5/225* | (2006.01) |
| *H04N 5/232* | (2006.01) |
| *G16H 20/13* | (2018.01) |
| *G16H 20/10* | (2018.01) |
| *F21Y 115/10* | (2016.01) |

(52) U.S. Cl.
CPC .............. *A61J 7/0076* (2013.01); *F21V 9/14* (2013.01); *G01G 19/414* (2013.01); *G06K 9/2018* (2013.01); *G06Q 10/06395* (2013.01); *G16H 20/10* (2018.01); *G16H 20/13* (2018.01); *G16H 40/63* (2018.01); *H04N 5/2252* (2013.01); *H04N 5/2256* (2013.01); *H04N 5/23216* (2013.01); *H04N 7/18* (2013.01); *H04N 7/183* (2013.01); *A47B 2037/005* (2013.01); *A61J 2200/74* (2013.01); *F21Y 2115/10* (2016.08)

(58) Field of Classification Search
CPC .... G16H 40/63; G01G 19/414; G06K 9/2018; G06Q 10/06395; G06Q 50/22; A47B 13/003; A47B 13/10; A47B 37/00; A47B 2037/005; H04N 5/2252; H04N 5/2256; H04N 5/23216; H04N 7/18; H04N 7/183; F21V 9/14; F21Y 2115/10
USPC ........................................................ 348/143
See application file for complete search history.

(56) References Cited

U.S. PATENT DOCUMENTS

| | | |
|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,526,574 A | 7/1985 | Pekkarinen |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustaysson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |

(56) References Cited

U.S. PATENT DOCUMENTS

| | | |
|---|---|---|
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,770,184 A | 9/1988 | Greene et al. |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | McIntosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,880,013 A | 11/1989 | Chio |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,905,163 A | 2/1990 | Garber et al. |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,943,987 A | 7/1990 | Asahina et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,964,847 A | 10/1990 | Prince |
| 4,966,579 A | 10/1990 | Polaschegg |
| 4,967,928 A | 11/1990 | Carter |
| 4,968,295 A | 11/1990 | Neumann |
| 4,975,647 A | 12/1990 | Downer et al. |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,103,211 A | 4/1992 | Daoud et al. |
| 5,104,374 A | 4/1992 | Bishko et al. |
| 5,108,131 A | 4/1992 | Nassim |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |

(56) References Cited

U.S. PATENT DOCUMENTS

| | | |
|---|---|---|
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,884 A | 11/1993 | Stern et al. |
| 5,262,943 A | 11/1993 | Thibado et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,747 A | 8/1994 | Neftel |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,360,410 A | 11/1994 | Wacks |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |

(56) References Cited

U.S. PATENT DOCUMENTS

| | | |
|---|---|---|
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,434 A | 10/1996 | Halperin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |

(56) References Cited

U.S. PATENT DOCUMENTS

| | | |
|---|---|---|
| 5,835,897 A | 11/1998 | Dang |
| 5,836,910 A | 11/1998 | Duffy et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toays et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,941,846 A | 8/1999 | Duffy et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,961,923 A | 10/1999 | Nova et al. |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,939 A | 11/1999 | Berman et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,023,539 A | 2/2000 | Blomquist |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |

(56) References Cited

U.S. PATENT DOCUMENTS

| | | |
|---|---|---|
| 6,081,048 A | 6/2000 | Bergmann et al. |
| 6,081,786 A | 6/2000 | Barry et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,177 A | 10/2000 | Venkatraman et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,213,972 B1 | 4/2001 | Butterfield et al. |
| 6,219,439 B1 | 4/2001 | Burger |
| 6,219,587 B1 | 4/2001 | Ahlin et al. |
| 6,221,009 B1 | 4/2001 | Doi et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,142 B1 | 5/2001 | Benigno et al. |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,021 B1 | 7/2001 | Wong et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,278,999 B1 | 8/2001 | Knapp |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,502 B1 | 11/2001 | Schoenberg et al. |
| 6,322,504 B1 | 11/2001 | Kirshner |
| 6,322,515 B1 | 11/2001 | Goor et al. |
| 6,330,491 B1 | 12/2001 | Lion |
| 6,332,090 B1 | 12/2001 | DeFrank et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,347,553 B1 | 2/2002 | Morris et al. |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,401,072 B1 | 6/2002 | Haudenschild et al. |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |

(56) References Cited

U.S. PATENT DOCUMENTS

| | | |
|---|---|---|
| 6,421,650 B1 | 7/2002 | Goetz et al. |
| 6,424,996 B1 | 7/2002 | Killcommons et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,461,037 B1 | 10/2002 | O'Leary |
| 6,463,310 B1 | 10/2002 | Swedlow et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,471,646 B1 | 10/2002 | Thede |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,494,831 B1 | 12/2002 | Koritzinsky |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,602,469 B1 | 8/2003 | Maus et al. |
| 6,607,485 B2 | 8/2003 | Bardy |
| 6,610,973 B1 * | 8/2003 | Davis, III ............... A61J 7/02 250/222.1 |
| 6,613,009 B1 | 9/2003 | Bainbridge et al. |
| 6,616,633 B1 | 9/2003 | Butterfield et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,669,663 B1 | 12/2003 | Thompson |
| 6,673,314 B1 | 1/2004 | Burbank et al. |
| 6,687,546 B2 | 1/2004 | Lebel et al. |
| 6,689,091 B2 | 2/2004 | Bui et al. |
| 6,694,191 B2 | 2/2004 | Starkweather et al. |
| 6,694,334 B2 | 2/2004 | Dulong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,887,201 B2 | 5/2005 | Bardy |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,265 B1 | 7/2005 | Johnson |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,240,699 B2 | 7/2007 | Osborne et al. |
| 7,255,680 B1 | 8/2007 | Gharib |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,321,861 B1 | 1/2008 | Oon |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,509,280 B1 | 3/2009 | Haudenschild |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,698,154 B2 | 4/2010 | Marchosky |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |

(56) References Cited

U.S. PATENT DOCUMENTS

| | | |
|---|---|---|
| 7,801,642 B2 | 9/2010 | Ansari et al. |
| 7,847,970 B1 | 12/2010 | McGrady |
| 7,853,621 B2 | 12/2010 | Guo |
| 7,904,822 B2 | 3/2011 | Monteleone et al. |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B1 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B1 | 11/2013 | Ansari |
| 8,666,541 B1 | 3/2014 | Ansari et al. |
| 8,678,047 B2 | 3/2014 | Tribble et al. |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| D753,428 S | 4/2016 | Shao |
| 9,362,969 B1 | 6/2016 | Burgess et al. |
| 9,382,021 B2 | 7/2016 | Tribble et al. |
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034614 A1 | 10/2001 | Fletcher-Haynes et al. |
| 2001/0034616 A1 | 10/2001 | Giannini |
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0047125 A1 | 11/2001 | Quy |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0007285 A1 | 1/2002 | Rappaport |
| 2002/0010568 A1 | 1/2002 | Rubbert et al. |
| 2002/0010679 A1 | 1/2002 | Felsher |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032582 A1 | 3/2002 | Feeney et al. |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0062227 A1 | 5/2002 | Yuyama |
| 2002/0062229 A1 | 5/2002 | Alban et al. |
| 2002/0065540 A1 | 5/2002 | Lebel et al. |
| 2002/0065686 A1 | 5/2002 | Monteleone et al. |
| 2002/0067273 A1 | 6/2002 | Jaques et al. |
| 2002/0072733 A1 | 6/2002 | Flaherty |
| 2002/0073250 A1 | 6/2002 | Ommering |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0091309 A1 | 7/2002 | Auer |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116226 A1 | 8/2002 | Auer et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0188467 A1 | 12/2002 | Eke |
| 2002/0198473 A1 | 12/2002 | Kumar et al. |
| 2002/0198513 A1 | 12/2002 | Lebel et al. |
| 2002/0198624 A1 | 12/2002 | Greenwald |
| 2003/0006878 A1 | 1/2003 | Chung |
| 2003/0023177 A1 | 1/2003 | Bardy |
| 2003/0033532 A1 | 2/2003 | Marks |
| 2003/0036783 A1 | 2/2003 | Bauhahn et al. |
| 2003/0046114 A1 | 3/2003 | Davies et al. |
| 2003/0046280 A1 | 3/2003 | Rotter et al. |
| 2003/0046439 A1 | 3/2003 | Manke et al. |
| 2003/0050621 A1 | 3/2003 | Lebel et al. |
| 2003/0050731 A1 | 3/2003 | Rosenblum |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0076736 A1 | 4/2003 | Buker et al. |
| 2003/0078534 A1 | 4/2003 | Hochman et al. |
| 2003/0079746 A1 | 5/2003 | Hickle |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0114836 A1 | 6/2003 | Estes et al. |
| 2003/0117580 A1 | 6/2003 | Franz et al. |
| 2003/0125609 A1 | 7/2003 | Becker |

(56) References Cited

U.S. PATENT DOCUMENTS

| | | |
|---|---|---|
| 2003/0125611 A1 | 7/2003 | Bardy |
| 2003/0139701 A1 | 7/2003 | White et al. |
| 2003/0144878 A1 | 7/2003 | Wilkes et al. |
| 2003/0149599 A1 | 8/2003 | Goodall et al. |
| 2003/0154108 A1 | 8/2003 | Fletcher-Haynes et al. |
| 2003/0158508 A1 | 8/2003 | DiGianfilippo |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0179287 A1 | 9/2003 | Kozic et al. |
| 2003/0181851 A1 | 9/2003 | Mann et al. |
| 2003/0182164 A1 | 9/2003 | Blomquist |
| 2003/0195397 A1 | 10/2003 | Bardy |
| 2003/0200117 A1 | 10/2003 | Manetta et al. |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2003/0231803 A1 | 12/2003 | Huang |
| 2004/0002874 A1 | 1/2004 | Shaffer et al. |
| 2004/0017475 A1 | 1/2004 | Akers et al. |
| 2004/0019607 A1 | 1/2004 | Moubayed et al. |
| 2004/0115132 A1 | 1/2004 | Brown |
| 2004/0039260 A1 | 2/2004 | Bardy |
| 2004/0039264 A1 | 2/2004 | Bardy |
| 2004/0051368 A1 | 3/2004 | Caputo et al. |
| 2004/0055611 A1 | 3/2004 | Penny et al. |
| 2004/0064343 A1 | 4/2004 | Korpman et al. |
| 2004/0073329 A1 | 4/2004 | Engleson |
| 2004/0088187 A1 | 5/2004 | Chudy et al. |
| 2004/0088374 A1 | 5/2004 | Webb et al. |
| 2004/0105271 A1* | 6/2004 | Chen .................. F21S 6/003 362/402 |
| 2004/0111293 A1 | 6/2004 | Firanek et al. |
| 2004/0116862 A1 | 6/2004 | Ray |
| 2004/0117215 A1 | 6/2004 | Marchosky |
| 2004/0128162 A1 | 7/2004 | Schlotterbeck et al. |
| 2004/0129616 A1 | 7/2004 | Mori et al. |
| 2004/0148195 A1 | 7/2004 | Kalies |
| 2004/0158193 A1 | 8/2004 | Bui et al. |
| 2004/0172283 A1 | 9/2004 | Vanderveen et al. |
| 2004/0172289 A1 | 9/2004 | Kozic et al. |
| 2004/0172300 A1 | 9/2004 | Mihai et al. |
| 2004/0181268 A1* | 9/2004 | Anderer .............. A61N 5/0619 607/90 |
| 2004/0193328 A1 | 9/2004 | Zaitsu et al. |
| 2004/0193453 A1 | 9/2004 | Butterfield et al. |
| 2004/0204673 A1 | 10/2004 | Flaherty |
| 2004/0204954 A1 | 10/2004 | Lacko |
| 2004/0215490 A1 | 10/2004 | Duchon et al. |
| 2004/0220829 A1 | 11/2004 | Baharav et al. |
| 2004/0225528 A1 | 11/2004 | Brock |
| 2004/0235446 A1 | 11/2004 | Flaherty et al. |
| 2004/0236630 A1 | 11/2004 | Kost et al. |
| 2004/0248295 A1 | 12/2004 | Katsuhiko et al. |
| 2004/0260233 A1 | 12/2004 | Garibotto et al. |
| 2004/0260577 A1 | 12/2004 | Dahlin et al. |
| 2005/0001033 A1 | 1/2005 | Cheong et al. |
| 2005/0017864 A1 | 1/2005 | Tsoukalis |
| 2005/0033124 A1 | 2/2005 | Kelly et al. |
| 2005/0033773 A1 | 2/2005 | Roberge et al. |
| 2005/0038680 A1 | 2/2005 | McMahon |
| 2005/0039742 A1 | 2/2005 | Hickle |
| 2005/0043665 A1 | 2/2005 | Vinci et al. |
| 2005/0045548 A1 | 3/2005 | Brugger et al. |
| 2005/0054923 A1 | 3/2005 | Pan |
| 2005/0060372 A1 | 3/2005 | DeBettencourt et al. |
| 2005/0080651 A1 | 4/2005 | Morrison et al. |
| 2005/0187794 A1 | 8/2005 | Kimak |
| 2005/0209737 A1 | 9/2005 | Kircher |
| 2005/0228238 A1 | 10/2005 | Monitzer |
| 2005/0279419 A1 | 12/2005 | Tribble et al. |
| 2006/0084042 A1 | 4/2006 | Weaver et al. |
| 2006/0124656 A1 | 6/2006 | Popovich, Jr. |
| 2006/0136095 A1 | 6/2006 | Rob et al. |
| 2006/0149416 A1 | 7/2006 | Mohapatra et al. |
| 2006/0161294 A1 | 7/2006 | DiMaggio |
| 2006/0173714 A1 | 8/2006 | Grotzinger, Jr. |
| 2006/0178578 A1 | 8/2006 | Tribble et al. |
| 2006/0181391 A1 | 8/2006 | McNeill et al. |
| 2006/0235881 A1 | 10/2006 | Masarie et al. |
| 2007/0043767 A1 | 2/2007 | Osborne et al. |
| 2007/0047980 A1 | 3/2007 | Limer et al. |
| 2007/0088568 A1 | 4/2007 | Goodall et al. |
| 2007/0110305 A1 | 5/2007 | Corcoran et al. |
| 2007/0125442 A1 | 6/2007 | Tribble et al. |
| 2007/0168228 A1 | 7/2007 | Lawless |
| 2007/0179806 A1 | 8/2007 | Knowlton et al. |
| 2007/0189597 A1 | 8/2007 | Limer et al. |
| 2007/0192139 A1 | 8/2007 | Cookson et al. |
| 2007/0216998 A1 | 9/2007 | Sander |
| 2007/0239482 A1 | 10/2007 | Finn et al. |
| 2007/0239997 A1 | 10/2007 | Qu et al. |
| 2008/0046292 A1 | 2/2008 | Myers et al. |
| 2008/0056556 A1 | 3/2008 | Eller et al. |
| 2008/0059228 A1 | 3/2008 | Bossi et al. |
| 2008/0091467 A1 | 4/2008 | Moncrief et al. |
| 2008/0119958 A1 | 5/2008 | Bear et al. |
| 2008/0125897 A1 | 5/2008 | DiGianfilippo et al. |
| 2008/0147554 A1 | 6/2008 | Stevens et al. |
| 2008/0195246 A1 | 8/2008 | Tribble et al. |
| 2008/0214333 A1* | 9/2008 | Peery .................. A63B 63/083 473/483 |
| 2008/0306926 A1 | 12/2008 | Friedlander et al. |
| 2009/0024414 A1 | 1/2009 | Mansour et al. |
| 2009/0080408 A1 | 3/2009 | Natoli et al. |
| 2009/0097368 A1 | 4/2009 | Vlutters et al. |
| 2009/0138340 A1 | 5/2009 | Borr et al. |
| 2009/0157537 A1* | 6/2009 | Miller .................. G06Q 10/109 705/32 |
| 2009/0188937 A1* | 7/2009 | Kim .................... A61J 7/0069 221/312 B |
| 2009/0189988 A1* | 7/2009 | Jia ...................... G05B 19/042 348/211.4 |
| 2009/0205877 A1 | 8/2009 | Claypool |
| 2009/0210252 A1 | 8/2009 | Silver |
| 2009/0235194 A1 | 9/2009 | Arndt et al. |
| 2009/0258331 A1 | 10/2009 | Do et al. |
| 2009/0285762 A1 | 11/2009 | Flower |
| 2009/0313044 A1 | 12/2009 | Haque et al. |
| 2009/0323170 A1 | 12/2009 | Lin |
| 2009/0324032 A1 | 12/2009 | Chen |
| 2010/0017031 A1 | 1/2010 | Rob et al. |
| 2010/0091281 A1 | 4/2010 | Suzuki |
| 2010/0094653 A1 | 4/2010 | Tribble et al. |
| 2010/0128165 A1 | 5/2010 | Newcomb et al. |
| 2010/0157293 A9 | 6/2010 | Rzasa et al. |
| 2010/0185456 A1 | 7/2010 | Kansal |
| 2010/0241270 A1 | 9/2010 | Eliuk et al. |
| 2011/0090350 A1* | 4/2011 | Oomori ................ H04N 5/2252 348/207.99 |
| 2011/0119088 A1 | 5/2011 | Gunn |
| 2011/0191121 A1 | 8/2011 | Fioravanti |
| 2011/0202366 A1 | 8/2011 | Akers et al. |
| 2011/0208350 A1 | 8/2011 | Eliuk et al. |
| 2011/0267465 A1 | 11/2011 | Alexander et al. |
| 2012/0097290 A1 | 4/2012 | Mikhaeil |
| 2012/0200596 A1 | 8/2012 | Gotou et al. |
| 2012/0211565 A1 | 8/2012 | Colavito |
| 2012/0303388 A1 | 11/2012 | Vishnubhatla et al. |
| 2013/0079581 A1 | 3/2013 | Agamaite et al. |
| 2013/0090947 A1 | 4/2013 | Nockley |
| 2013/0197445 A1 | 8/2013 | Schabbach et al. |
| 2013/0262138 A1 | 10/2013 | Jaskela et al. |
| 2013/0279774 A1 | 10/2013 | Helgason et al. |
| 2013/0304510 A1 | 11/2013 | Chan et al. |
| 2013/0314535 A1 | 11/2013 | Yuyama et al. |
| 2013/0342676 A1 | 12/2013 | Amano |
| 2014/0022569 A1 | 1/2014 | Matsui et al. |
| 2014/0156064 A1 | 6/2014 | Crawford et al. |
| 2014/0156294 A1 | 6/2014 | Tribble et al. |

(56) References Cited

U.S. PATENT DOCUMENTS

| | | |
|---|---|---|
| 2014/0214436 A1 | 7/2014 | Utech et al. |
| 2014/0350950 A1 | 11/2014 | Jaskela et al. |
| 2015/0205932 A1 | 7/2015 | Tribble |
| 2015/0227719 A1 | 8/2015 | Ranalletta |
| 2015/0272320 A1 | 10/2015 | Ranalletta et al. |
| 2015/0278477 A1 | 10/2015 | Tribble |
| 2015/0286799 A1 | 10/2015 | Padmani |
| 2016/0072985 A1 | 3/2016 | Sandmann et al. |
| 2016/0092638 A1 | 3/2016 | Padmani |
| 2016/0092639 A1 | 3/2016 | Padmani |
| 2016/0140315 A1 | 5/2016 | Diaz et al. |
| 2016/0210437 A1 | 7/2016 | Padmani et al. |
| 2016/0371462 A1 | 12/2016 | Wallen |
| 2017/0372034 A1 | 12/2017 | Tribble |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1072994 | 2/2001 |
| EP | 1107158 A1 | 6/2001 |
| EP | 1097671 | 2/2003 |
| EP | 2489343 A1 | 8/2012 |
| GB | 994977 | 6/1956 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 53137644 | 12/1978 |
| JP | 61066950 | 4/1986 |
| JP | 63068133 | 3/1988 |
| JP | 2111375 | 4/1990 |
| JP | 3423055 B2 | 1/1994 |
| JP | 6086813 | 3/1994 |
| JP | 06327636 | 11/1994 |
| JP | 7-204253 A | 8/1995 |
| JP | 07204253 A | 8/1995 |
| JP | 104585 | 1/1998 |
| JP | 10014890 | 1/1998 |
| JP | 10079770 | 3/1998 |
| JP | 2000036032 A | 2/2000 |
| JP | 03055131 | 4/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |
| JP | 2004340770 A | 12/2004 |
| JP | 2005252710 A | 9/2005 |
| JP | 2006033291 A | 2/2006 |
| JP | 2006334062 | 12/2006 |
| JP | 2006334062 A | 12/2006 |
| JP | 2007151001 A | 6/2007 |
| JP | 2007198934 A | 8/2007 |
| JP | 2008-139201 A | 6/2008 |
| JP | 2008139201 A | 6/2008 |
| JP | 4276654 B2 | 6/2009 |
| JP | 2009265827 A | 11/2009 |
| JP | 2010056619 A | 3/2010 |
| JP | 2010170504 A | 8/2010 |
| JP | 2010533927 A | 10/2010 |
| JP | 2011151430 A | 8/2011 |
| JP | 2012-078265 A | 4/2012 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |
| WO | 2012056317 A2 | 5/2012 |

OTHER PUBLICATIONS

Parsons, et al., "Digital Media—Can I Change a Graphic's File Size?", New Perspectives on Computer Concepts—Course Technology, 2011, Cengage Learning, Boston, MA.

Phillips, Jon, Associate Director of Telemedicine; "Telepharmacy at Texas Tech," presented Apr. 30, 2003, published at http://www.ttuhsc.edu/telemedicine/publ cation.htm at least by Jun. 22, 2003 Jun. 22, 2003.

Texas Administrative Code, Title 22, Part 15, Ch 291, Rules 20, 36, and 71-74. Feb. 10, 2004.

Peterson, Charles D. and Anderson, Jr, Howard C.; "The North Dakota Telepharmacy Project: Restoring and Retaining Pharmacy Services in Rural Communities" Feb. 1, 2004.

Cato Reference Manual, Support for Trial Version (Abridged), Vienna, May 2004 Jun. 1, 2004.

Seifert et al.; "The Training of a Telepharmacist: Addressing the Needs of Rural West Texas," American Journal of Pharmaceutical Education 2004; 68 (3) Article 60. Jul. 16, 2004.

Cato Reference Manual, Vienna, May 2005 May 1, 2005.

"The World's First Fully Integrated Workflow Manager for I.V. Rooms", IntelliFlowRx Brochure, ForHealth Technologies, Inc., United States, May 2008.

Baxa Corporation, DoseEdge the Leading Edge in Dose Management, Brochure, published copyright date 2010.

Baxa Corporation, Product Catalog 2010-2011, published at least by Sep. 15, 2012, https:l/web.archive.org/Web/20120915210739/http://www.baxa.com/resources/docs/BaxaCatalog.pdf.

AHRQ Health Information Technology Program—Update Jun. 2005 Fact Sheet,, http://www.ahrq.gov/research/findings/factsheets/it/hitfact/index.html—3 pages.

(56) References Cited

OTHER PUBLICATIONS

Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.
Allan T. Pryor, "Current State of Computer-based Patient Record Systems," Aspects of the Computer-based Patient Record, 1992, pp. 67-82, Springer-Verlag, New York, NY.
Anderson, Howard "A Narrative on the History of the Development of Telepharmacy in North Dakota from the Board of Pharmacy's Perspective Recorded by Excerpts from Board Minutes", Feb. 2006.
Angaran, "Telemedicine and telepharmacy: Current status and future implications", Am J Health-Syst Pharm, vol. 56, Jul. 15, 1999, pp. 1404-1405.
Ann Slone Endo, "Using Computers in Newborn Intensive Care Settings," American Journal of Nursing, Jul. 1981, pp. 1336-1337.
Anonymous, "Chains covet customized pharmacy integration" Drug Store New, Aug 18, 2003, vol. 25, No. 10—p. 73.
Automated Dispensing Technologies: Directory of Vendors, http://pharmacyautomation.com/vendors.html, Jun 5, 2003—3 pages.
Auto Syringe® AS40A Infusion Pump Technical Manual, 1995, 89 pages, Baxter Healthcare Corporation, Deerfield, IL.
Baxa Corporation, DoseEdge the Leading Edge in Dose Management, Brochure, published copyright date 2010—5 pages.
Baxa Corporation, Product Catalog 2010-2011, published at least by Sep. 15, 2012, https://web.archive.org/web/20120915210739http://www.baxa.com/resources/docs/BaxaCatalog.pdf (52 pages).
Bell Atlantic Healthcare Systems, Inc., court exhibit, StatLan Functions and Features, Specification, release 3.5, dated Nov. 12, 1992, 49 pages.
Ben Schneiderman, "Designing the User Interface: Strategies for Effective Human-Computer Interaction," 2d Ed., 1992, Chapter 5: Direct Manipulation (56 pages), Addison-Wesley Publishing Company.
"Block Medical: Growing with Home Infusion Therapy," taken from Invivo, the Business and Medicine Report, Apr. 1991, pp. 7-9.
Bynum et al., "The Effect of Telepharmacy Counseling on Metered-Dose Inhaler Technique among Adolescents with Asthma in Rural Arkansas", Telemedicine Journal and e-health, vol. 7, No. 3, 2001, Mary AnnLiebert, Inc., pp. 207-218.
Cabral, Jr. et al., "Multmedia Systems for Telemedicine Systems for Telemedicine and Their Communications Requirements," IEEE Communications Magazine Jul. 1996, pp. 20-27.
Cardinal Health Introduces Rxe-source(SM) to Address Pharmacist Labor Shortage and Medication Safety Challenges at Hospitals. PR Newswire, Feb. 25, 2003—5 pages.
Casey, Michelle M. et al., "Pharmacist Staffing and the Use of Technology in Small Rural Hospitals: Implications for Medication Safety" Upper Midwest Rural Health Research Center, Dec. 2005—51 pages.
Charles Safran, M.D. et al., "Computer-Based Support for Clinical Decision Making," Clinical Computin, vol. 7, No. 5 (1990), pp. 319-322.
Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.
Clement J. McDonald, M.D. et al, "The Three-Legged Stool: Regenstrief Institute for Health Care," Third Annual Nicholas E. Davies Award Proceedings of the CPR Recognition Symposium, 1997, pp. 131-158, Computer-based Patient Record Institute, Inc., Bethesda, MD.
Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.

Clifton, G. Dennis et al., "Provision of pharmacy services to underserved populations via remote dispensing and two-way videoconferencing" Am J Health-Syst Pharm, vol. 60, Dec. 15, 2003 oe pp. 2577-2582.
Dan Murphy, "Nuclear Pharmacy Primer", Radiation Protection Management, vol. 20, No. 5 (2003), pp. 1-10.
Dan Scheraga; "Tech firms answer chain pharmacy's call for productivity," Drug Store News; Dec. 15, 2003; 25, 17; ProQuest Research Library, p. 31-32.
Daniel Andresen et al., "Scalability Issues for High Performance Digital Libraries on the World Wide Web," Proceedings of ADL '96, 1996, pp. 139-148, IEEE.
Daniel J. Nigrin et al., "Glucoweb: A Case Study of Secure, Remote Biomonitoring and Communication," Proceedings of the 2000, 5 pages, American Medical Informatics Association, Bethesda, MD.
Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.
Dart, Luann, "Digital Doses" Rural Electric, Jan. 2005—pp. 28-31.
Deborah J. Mayhew, "Principles and Guidelines in Software user Interface Designs," 1992, selected portions of Chapter 9, 17 pages, Prentice- Hall, Inc.
Defendants Initial Invalidity Contentions with Exhibits A and B dated Sep. 8, 2014; Civil Action No. 1:14-cv-00222.
Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.
Donna Young; "Loan repayments help pharmacists provide care in medically underserved areas," American Journal of Health-System Pharmacy; Nov. 1, 2003, pp. 2186-2188, vol. 60.
Environmental Scan of Pharmacy Technicians; M. MacInnis; Canadian Pharmacists Association; Sep. 2001.
Exhibit 1, Publications Manually Reviewed for the Search to U.S. Pat. No. 8,347,887 titled "System and Method for Remotely Supervising and Verifying Pharmacy Functions" As of Jun. 25, 2014.
Exhibit 1001 U.S. Pat. No. 8,374,887, Alexander issued Feb. 12, 2013.
Exhibit 1005, 22 TAC §§291.20, 291.36, and 291.71-291.74 date issued Mar. 5, 2015 from U.S. Pat. No. 8,374,887.
Exhibit 1006 U.S. Pat. No. 6,711,460 Reese issued Mar. 23, 2004 from U.S. Pat. No. 8,374,887.
Exhibit 1009, Peterson et al., The North Dakota Telepharmacy Project: Restoring and Retaining Pharmacy Services in Rural Communities; the journal of Pharmacy Technology, vol. 20, No. 1, Jan./Feb. 2004- pp. 1-39 from U.S. Pat. No. 8,374,887.
Exhibit 1011, Complaint—*Alexander* v. *Baxter*, (W.D.Texas 2014) filed Mar. 13, 2014 from U.S. Pat. No. 8,374,887.
Exhibit 1012, Charles F. Seifert et al., "The Training of a Telepharmacist: Addressing the Needs of Rural West Texas," American Journal of Pharmaceutical Education, 2004; 68 (3) Article 60—pp. 1-9 from U.S. Pat. No. 8,374,887.
Exhibit 1017, Declaration of Dr. Roger W. Anderson in Support of Becton, Dickinson & Company's Response to Baxter's Motion for Summary Judgment of Invalidity Based Upon 35 U.S.C. § 101 filed Jan. 15, 2015 from U.S. Pat. No. 8,374,887.
Exhibit 1018, Plaintiff's Claim Construction Brief, 1:14-cv-222-LY filed Oct. 17, 2014 from U.S. Pat. No. 8,374,887.
Exhibit 1019, Plaintiff's Reply Claim Construction Brief, 1:14-cv-222-LY filed Nov. 7, 2014 from U.S. Pat. No. 8,374,887.
Exhibit 1020, The United States Pharmacopeia—the Official Compendia of Standards; 2004 from U.S. Pat. No. 8,374,887.
Exhibit 1023, Charles D Peterson et al., "The North Dakota Telepharmacy Project: Restoring and Retaining Pharmacy Services in Rural Communities," J Pharm Technol, 2004; vol. 20—pp. 028-039 from U.S. Pat. No. 8,374,887.
Exhibit 1025, Affidavit of Christopher Butler with attached Telemedicine Report Archive dated Mar. 4, 2015—6 pages from U.S. Pat. No. 8,374,887.

(56) References Cited

OTHER PUBLICATIONS

Exhibit 1026, Affidavit of Christopher Butler with attached presentation Telepharmacy at Text Tech—Jon Phillips dated Mar. 4, 2015—31 pages from U.S. Pat. No. 8,374,887.
Exhibit 1027, Order on Motion for Summary Judgment filed Aug. 3, 2015 from U.S. Pat. No. 8,374,887.
Exhibit 1028, Final Judgment filed Aug. 3, 2015 from U.S. Pat. No. 8,374,887.
Exhibit 1030 Deposition of Charles Seifert Dec. 4, 2015 from U.S. Pat. No. 8,374,887.
Exhibit 1031 Deposition of Diane B. Ginsburg, PhD. Dec. 16, 2015 from U.S. Pat. No. 8,374,887.
Exhibit 1032 Texas Administrative Code, Title 22, Chapter 291, Subchapter A, Section 291.23 as in effect on Feb. 1, 2004 from U.S. Pat. No. 8,374,887.
Felkey, Bill G., "Integrating Technology at the Point of Care", Insight, Jan. 2004—pp. 8-10.
Formula for Patient Safety; ScriptPro; Aug. 17, 2003.
Fred Puckett, "Medication-management component of a point-of-care information system," Am. J. Health-Syst.Pharm., Jun. 15, 1995, pp. 1305-1309, vol. 52, American Society of Health-System Pharmacists, Inc.
"GE ImageQuant TL 7.0 Image Analysis Software" User Manual, May 2007, http://nba.uth.tmc.edu/Assets/pdf/other/typhoon—supporting—files/IQTL—UserManual.pdf, Uppsala, Sweden.
Gerald E. Meyer et al., "Use of bar codes in inpatient drug distribution," Am. J. Hosp. Pharm., May 1991, pp. 953-966, vol. 48, American Society of Hospital Pharmacists, Inc.
Ghent, Natale, "Pharmacists go digital to fight shortage", Pharmacy Practice 20.11 (Nov. 2004): 47—2 pages.
Gilad J. Kuperman, M.D. et al., "Innovations and research review: The impact of the HELP computer system on the LDS Hospital paper medical record," Topics in Health Record Management, 1991, pp. 76-85, vol. 12, Issue 2, Aspen Publishers, Inc.
"Global Med Announces First Safetrace TX™ Sale," Apr. 1, 1999, 2 pages.
Global Med Technologies, Inc. Introduces PeopleMed™.com, inc., a Chronic Disease Management Application Service Provider (ASP) Subsidiary, Jan. 11, 2000, 2 pages, Global med Technologies, Inc., Denver, CO.
Gretchen A. Barry et al., "Bar-code technology for documenting administration of large-volume intravenous solutions," American Journal of Hospital Pharmacy, Feb. 1989, pp. 282-287, vol. 46, American Society of Hospital Pharmacists.
H. Paul Hammann et al., "A World Wide Web Accessible Multi-Species ECG Database," 1997, pp. 7-12, ISA.
Henry J. Lowe et al., "WebReport: A World Wide Web Based Clinical Multimedia Reporting System," 1996, pp. 314-318, Amia, Inc.
"Hospitals battle errors with bar codes," Mar. 24, 2004, 3 pages, MSNBC.
Howard L. Bleich et al., "Clinical Computing in a Teaching Hospital," Use and Impact of Computers in Clinical Medicine, 1987, pp. 205-223 and selected pages, Springer-Verlag, New York, NY.
http://isorx.com/ Jan. 29, 2004.
http://www.scriptpro.com/products//sp-200/main.htm, Feb. 13, 2004, Product listing for SP 200® Robotic Prescription Dispensing System.
http://www.scriptpro.com/products/space/space200.htm, Feb. 10, 2004, Product listing for SP Automation Center 200TM (Space 200TM) Prescription Dispensing Automation Center.
Hughes, Shirley, "Bedside Terminals: Clinicom," Clinical Computing, Jan./Feb. 1988, pp. 22-28, vol. 5, No. 1.
IPR Decision Paper No. 8 Entered Aug. 13, 2015 from U.S. Pat. No. 8,374,887.
IPR Final Written Decision Paper No. 29 Entered Jul. 11, 2016 from U.S. Pat. No. 8,374,887.
James Kazmer et al., "The Creation of Virtual Electronic Medical Record," 1996, 17 pages.
Jennifer Langham; "Taking Automation to New Levels," Insight, the QS/1 Magazine, Oct. 2002; pp. 2-5.
John Frady; "What's New in RxCare Plus 17.2," Insight, the QS/1 Magazine, Apr. 2002; pp. 2-3, 14.
Jones, et al., "Use of a remote computerized system for study documentation in clinical trials" Drug Information Journal, Oct.-Dec. 1998, vol. 32, No. 4 oe pp. 1153-1163.
Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.
Kastango, Eric S. and Bradshaw, Brian D., "USP chapter 797: Establishing a practice standard for compounding sterile preparations in pharmacy" Am J Health-Syst Pharm., Sep. 15, 2004, vol. 61—pp. 1928-1938.
Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.
Keeys, Christopher A. et al., "Providing nighttime pharmaceutical services through telepharmacy" Am J Health-Syst Pharm, Apr. 15, 2002, vol. 59—pp. 716-721.
Khan, Shamima et al., "Is There a Successful Business Case for Telepharmacy?" Telemedicine and e-Health, vol. 14, No. 3, Apr. 2008, pp. 235-245.
Kimber, Michael B. et al., "Telepharmacy-Enabling Technology to Provide Quality Pharmacy Services in Rural and Remote Communities" Journal of Pharmacy Practice and Research, vol. 36, No. 2, 2006—128-133.
Kosub, David, "Device allows pharmacy care in remote areas" Pharmacy Practice, vol. 20, No. 10, Oct. 2004—pp. 12-13.
Koutnik, Eileen, Assistnat Editor, Pharmacy Times, "The Pharmacy of Tomorrow" Pharmacy Times, Aug. 1, 2003—3 pages.
Larry B. Grandia, B.S.E. et al., "Building a computer-based Patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.
Lefkowitz, Sheldon et al., "A Trial of the Use of Bar Code Technology to Restructure a Drug Distribution and Administration System," 1991, pp. 239-242, Hospital Pharmacy, vol. 26.
LP, "ATM-STyle Drug Dispensers Taking Hold in Areas With Limited Pharmacist Services" Pharmacy Practice News, Jan. 2004, vol. 31, No. 1—4 pages.
"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.
Lustig, Ahuva, "Medication error prevention by pharmacists—an Israeli solution" Pharmacy World & Science, 2000, vol. 22, No. 1—pp. 21-25.
Medicaid Memo—Department of Medical Assistance Services (Converting NDCs from 10-digits to 11-digits) May 31, 2007.
Michael H. MacKin, "Impact of Technology on Environmental Therapeutic Device Design," Medical Instrumentation, Feb. 1987, pp. 33-35, vol. 21, No. 1, Association for the Advancement of Medical Instrumentation.
Michelle M. Casey, M.S., Jill Klingner, R.N., M.S., and Ira Moscovice, Ph.D.; "Access to Rural Pharmacy Services in Minnesota, North Dakota, and South Dakota," Working Paper Series, Jul. 2001, #36.
Monane et al., "Improving Prescribing Patterson for the Elderly Through an Online Drug Utilization Review Intervention", JAMA, Oct. 14,1998, vol. 280, No. 14—pp. 1249-1252.
Morris, Aisha M., Schneider, Philip J., Pedersen, Craig A. and Mirtallo, Jay M. "National survey of quality assurance activities for pharmacy-compounded sterile preparations" Am J Health-Syst Pharm, Dec. 15, 2003, vol. 60—pp. 2567-2576.
Murray, Michael D. et al. "Effects of Computer-based Prescribing on Pharmacist Work Patterns" Journal of the American Medical Informatics Association, Nov./Dec. 1998, vol. 5, No. 6—pp. 546-553.

(56) References Cited

OTHER PUBLICATIONS

Napoli, M. et al., "Picture archiving and communication in radiology", Rays. Jan.-Mar. 2003—PubMed—NCBI http://www.ncbi.nlm.m=nih.gov/pubmed/14509181—Abstract.
Nissen et al., Can telepharmacy provide pharmacy services in the bush, School of Pharmacy, University of Queensland, Brisbane, Australia, Journal of Telemedicine and Telecare 2003, vol. 9 (Suppl. 2): S2:39-41.
Parks, Liz, "Annual report of retail pharmacy: Using central-fill to maximize dispensing" Drug Store News, Aug. 20, 2001 vol. 24, No. 11—pp. 51, 75.
Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.
Paul H. Perlstein et al., "Future Directions for Device Design and Infant Management," Medical Instrumentation, Feb. 1987, pp. 36-41, vol. 21, No. 1, Association for the Advancement of Medical Instrumentation.
PCA II Multi-Mode Cartridge Operator's Manual, Sep. 1995, approx. 40 pages, Baxter Healthcare Corporation, Deerfield, IL.
Pesce, James, "Bedside Terminals: Medtake," Clinical Computing, Jan. /Feb. 1988, pp. 16-21, vol. 5, No. 1.
Peter Lord et al., MiniMed Technologies Programmable Implantable Infusion System, Annals New York Academy of Science, pp. 66-71, describing clinical trials from Nov. 1986.
Pharmacy Data Management (PDM) Technical Manual/Security Guide Version 1.0, Sep. 1997—55 pages.
Pharmacy education and practice out of sync? (Roundtable) Chain Drug Review, vol. 25, No. 6, Mar. 17, 2003, RX2 (6).
Prem S. Chopra, Virgil A. Thomason, and Dell M. Stinett; "Voice-Activated Networked Workstation for a Physically Disabled Physician," Oct. 7803-2050-6/94 1994 IEEE, pp. 478-479.
Product literature, Baxter Healthcare Corporation, "Flo-Gard® 6201 Volumetric Infusion Pump," 1992, 2 pages.
Product literature, Baxter Healthcare Corporation, "MultiPlex™ Series 100 Fluid Management System," 1988, 2 pages.
Remote Dispensing Regulations, NABPLAW Sep. 2003.
Woodall, Sandra C., Remote Order Entry and Video Verification; Reducing After-Hours Medication Errors in a Rural Hospital; S. Woodall; Joint Commission on Accreditation of Healthcare Organizations; vol. 30; No. 8; Aug. 2004.
Rich Muller; "NRx QS/1's Premium Pharmacy Software," Insight, the QS/1 Magazine, Jul. 2003; pp. 2-3, 12-15.
Rouse, et al., Academy of Managed Care Pharmacy et al., "White paper on pharmacy technicians 2002: Needed changes can no longer wait" Am J Health-Syst Pharm, Jan. 1, 2003, vol. 60—pp. 37-51.
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Clinical Observations Between Independent Computer Systems, Annual Book of ASTM Standards, Jun. Mar. 1994, pp. 132-210, E 1238-94, Philadelphia, PA.
Standard Specification for Transferring Clinical Observations Between Independent Computer Systems, Aug. 10, 1997, 79 pages, ASTM E 1238-97, West Conshohocken, PA, United States.
Standard Specification for Transferring Information Between Clinical Instruments and Computer Systems, Annual Book of ASTM Standards, Jun. 1991, 15 pages, E 1394-91, Philadelphia, PA.
Suzanne Carter, RN, Ed.D. et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.
T. Allan Pryor et al., "help—a Total Hospital Information System," Proceedings of the Fourth Annual Symposium on Computer Applications in Medical Care, Nov. 2-5 1980, pp. 3-7, vol. 1, Institute for Electrical and Electronics Engineers, New York, NY.
T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.
"Telepharmacy project expands students' practice experience" Telemedicine Report, vol. 6, No. 1, Jan. 2004 oe 4 pages.
Title 22. Examining Boards, 22 TAC Section 1.161; texinfo.library.unt.edu/Texasregister/html/2001/sep-14/PROPOSED/22.EXAMING BOARDS.html—Sep. 20, 2014, pp. 1-70.
Ukens, Carol, "Pharmacist shortage boosts telepharmacy" Drug Topoics, Jun. 3, 2002; 146, 11—p. 53.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
"Victor J. Perini et al., ""Comparison of automated medication-management systems,: Am. J. Hosp. Pharm., Aug. 1, 1994, pp. 1883-1891, vol. 51, American Society of Hospital Pharmacists, Inc."
Vincenzo Della Mae et al., "HTML generation and semantic markup for telepathology," Computer Networks and ISDN Systems, 1996, pp. 1085-1094, vol. 28, Elsevier Science B.V.
Website information for Cartharsis Medical Technology Products, Dec. 9, 2001, 15 pages.
Website information for MedPoint™, Mar. 13, 2003, 20 pages, Bridge Medical, Solana Beach, CA.
William R. Dito et al., "Bar codes and the clinical laboratory: adaptation perspectives," Clinical Laboratory Management Review, Jan./Feb. 1992, pp. 72-85, Clinical Laboratory Management Association, Inc.
Wills, Robert D., "Drug Images and Drug Imprints" Insight, Apr. 2001—p. 7.
Yvonne Mari Abdoo, "Designing a Patient Care Medication and Recording System that Uses Bar Code Technology," Computers in Nursing, May/Jun. 1992, pp. 116-120, vol. 10, No. 3.
Jon Phillips, Telepharmacy at Texas Tech, PowerPoint, Jan. 26, 1997, https://web.archive.org/web/20040509162423/http:/www.ttuhsc.edu/telemedicine/Powerpoint/Telepharmacy%20presentation%2042503.ppt.
A.H. McMorris et al. "Are Process Control Rooms Obsolete?", Control Engineering, pp. 42-47, Jul. 1971.
Standard Specification for Transferring Clinical Observations between Indepdendent Computer Systems, Annual Book of ASTM Standards, Nov. 14, 1991, pp. 1-64, ASTM E 1238-91,Philadelphia, PA.
Standard Specification for Transferring Information Between Clinical Instruments and Computer Systems, Dec. 10, 1997; 15 pages, ASTM E 1394-97, West Conshohocken, PA, United States.
Web site information, Information Data Management, Inc.'s PCMS: Plasma Center Management System, Dec. 14, 2001, 11 pages.
Specification for Low-Level Protocol to Transfer Messages Between Clinical Laboratory Instruments and Computer Systems, Mar. 11, 1991; 7 pages, ASTM E 1381-91, Philadelphia, PA, United States.
Atherton, H.D., Dollberg, S., Donnelly, M.M., Perlstein, P. H. Roath, S.B., "Computerized Temperature Control of the Low-Birth-Weight Infant: A 20-Year Retrospective and Future Prospects," Biomedical Instrumentation and Technology, Jul./Aug. 1994, pp. 302-309, vol. 28 No. 4.
Friesdorf, W., Grob-Alltag, F., Konichezky, S., Schwilk, B., Fattroth, A., Fett, P., "Lessons learned while building an integrated ICU workstation," International Journal of Clinical Monitoring and Computing, 1994, pp. 89-97, vol. 11.
Gammon, K., Robinson, K., "Bedside Data System Aids Pharmacy," Computers in Healthcare, Dec. 1988, pp. 35-37, vol. 9 No. 12.
Kampmann, J., Lau, G., Kropp, St., Schwarzer, E., Hernandez Sande, C., "Connection of electronic medical devices in ICU according to the standard 'MIB'," International Journal of Clinical Monitoring and Computing, 1991, pp. 163-166, vol. 8.
Angaran, "Telemedicine and telepharmacy: Current status and future implications", Am J Health-Syst Pharm, vol. 56, Jul. 15, 1999 (32 pages).
Carson, Ewart et al., "A Systems Methodology for the Development and Evaluation of a Telematic Home Haemodialysis Service," Proceedings—19th International Conference—IEEE/EMBS Oct. 30-Nov. 2, 1997, Chicago, Illinois, pp. 907-910.

(56) References Cited

OTHER PUBLICATIONS

Extended European Search Report dated Feb. 2, 2019, issued in related European Patent Application No. 18200417.6; 7 Pages.
Australian Examination Report for related Australian Application No. 2019208270; action dated Feb. 7, 2020; (6 pages).

* cited by examiner

WORK STATION FOR MEDICAL DOSE PREPARATION SYSTEM

RELATED APPLICATIONS

This application is a continuation of U.S. patent application Ser. No. 15/193,494, having a filing date of Jun. 27, 2016, entitled "WORK STATION FOR MEDICAL DOSE PREPARATION SYSTEM", which is a continuation of U.S. patent application Ser. No. 14/438,559, now U.S. Pat. No. 9,375,079, having a 371(c) filing date of Apr. 24, 2015, entitled "WORK STATION FOR MEDICAL DOSE PREPARATION SYSTEM," which is a U.S. National Stage of International Patent Application No. PCT/US2013/032545, filed Mar. 15, 2013, entitled "IMPROVED WORK STATION FOR MEDICAL DOSE PREPARATION SYSTEM," which claims the benefit of and priority to U.S. Provisional Patent Application No. 61/719,256 filed Oct. 26, 2012, entitled "WORK STATION FOR MEDICAL DOSE PREPARATION SYSTEM," all of which foregoing patent applications are incorporated herein by reference in their entirety.

BACKGROUND OF THE INVENTION

Many care providers have a pharmacy that prepares medical doses for administration to patients that are treated by the care provider. In this regard, the pharmacies may employ a formulary to prepare medications in order to fulfill medical dose orders that are ordered by care provider personnel (e.g., physicians) for administration to patients. Some medical doses to be prepared may include compounded sterile products (CSPs) that may be prepared in specially constructed and controlled environment (e.g., an "IV Room") in the pharmacy. The process of preparing medical doses may be carried out in accordance with local policy, governmental regulations, industry organizations (e.g., Chapter <797> of the United States Pharmacopoeia), or other applicable policies. For example, the preparation of medications may generally occur in a laminar airflow hood, isolator, or biological safety cabinet, by an operator (typically a pharmacy technician) who is tasked with preparing the medical doses. Once the medical doses are prepared, the medical doses may be required to be verified by a pharmacist prior to being dispensed from the pharmacy for administration to a patient.

In traditional pharmacy management techniques, medical dose orders may be provided to a printer that prints labels indicative of the medical dose order that are to be applied to finished doses once the doses are prepared. A pharmacy technician may be required to retrieve labels from a label printer and use those labels as work order travelers in the process of preparing each dose. Once the dose prepared, the technician may apply a label to the dose. The completed, labeled dose may be set aside for a pharmacist to check along with, for example, source ingredients, medicament receptacles used in the course of preparing the dose, and/or other material. In this regard, in order to check a dose, the pharmacist may be required to enter the clean room in which the doses are prepared and physically observe the materials associated with the dose order. As such, the checking of prepared doses may require the pharmacist to dress in protective clothing or equipment, which takes time and resources.

Furthermore, the only prompt a pharmacy may receive to prepare a medical dose order is the printing of the label. In this regard, if a label becomes lost or damaged, a dose may not be prepared. Additionally, prioritizing work also becomes difficult because the label stack at the label printer may be the only evidence of what doses have been ordered, prepared, and/or dispensed. As such, relying on physical labels alone to track doses may result in unprepared, lost, or duplicate doses. In some cases, pharmacies may produce duplicate labels as a matter of course such that the pharmacy must review each label against the other, already received labels, to determine if a label represents a new dose order that needs to be prepared. This practice may lead to increased administrative overhead in the pharmacy that add operational costs and reduce pharmacy efficiency.

Furthermore, while instructions for preparation of a drug may be recorded in official FDA-approved literature for the drug, pharmacy technicians may not reliably consult the literature when preparing doses. Rather, pharmacy technicians may memorize the steps needed for the most common drugs, and then generalize those steps to other drugs to be prepared without verifying the protocols associated with a particular drug. In this regard, if the dose order includes special instructions that a pharmacy technician does not recognize, references regarding the proper techniques may not be present or may not be consulted. Accordingly, dose orders including special instructions often must be prepared by more experienced technicians or at the direction of more experienced technicians. In either regard, the protocol used to prepare the dose may not conform to the FDA-approved literature for the drug being prepared.

Further still, in traditional pharmacy management techniques, the pharmacy technician may be responsible for creating records that are maintained in relation to doses that have been prepared and products from the formulary that were employed to make the dose. For example, a pharmacy technician may be tasked with transcribing information such as lot numbers, expiration dates, serial numbers, or the like. The manual creation of records requires labor intensive practices that may result in pharmacy inefficiencies, introduces the potential for errors in the records, and may result in virtually unsearchable paper records.

SUMMARY OF THE INVENTION

Embodiments of medical dose preparation management systems that may assist in management of medical doses are described herein. The embodiments described herein may include one or more work stations that are used to assist in preparation of a medical dose order. For example, the work stations may be used to provide guidance to a technician regarding the preparation of a medical dose order, and/or the work order stations may be used to capture, collect, or compile data (e.g., metadata) regarding the medical dose order. In this regard, metadata associated with the medical dose order may be stored in corresponding relation to the medical dose order such that the metadata may be accessible to a care provider before or after administration of the medical dose associated with the medical dose order to the patient. The metadata may include data regarding the prepared dose order, a component of the dose order, or the manner in which the prepared dose order or a component of the dose order was prepared. Accordingly, metadata captured, collected, or compiled at the work station may be used to organize, track, or otherwise manage medical dose orders. As such, examples of advantages facilitated by the medical dose preparation management system may include, among others, improved prioritization, organization, tracking, and records keeping for medical dose orders.

For example, the metadata regarding a dose order may include one or more medical dose preparation images related to components of a medical dose order, steps carried out during the preparation of a dose order, or a finished dose order. In this regard, the medical dose preparation images may be used to document or evidence the preparation of a medical dose order. It may be appreciated that the quality of the medical dose preparation images obtained by the medical dose preparation management system may be an important consideration in the medical dose preparation management system.

As such, it is presently recognized that the features and/or attributes of the work station may contribute to the accuracy, speed, and or quality at which the medical dose orders may be prepared by technicians at the work station while capturing, collecting, and/or compiling metadata (e.g., including medical dose preparation image data). As such, an objective of the present disclosure is to present work stations that facilitate efficient work flows to enable a technician to efficiently prepare medical dose orders while obtaining dose order metadata. Additionally, an objective of the present disclosure is to present work stations that facilitate the capture of high quality medical dose preparation images comprising dose order metadata. In this regard, the efficient capture of high quality dose order metadata during the preparation of a medical dose may contribute to patient safety, improve pharmacy efficiency, assist in pharmacy management, and/or provide other advantages as may be appreciated in the description presented herein. Furthermore, an objective of the present disclosure is to present work stations that may facilitate advantages related to administrative task performed at the work station such as work station cleaning.

Accordingly, a number of aspects are described herein that are related to a medical dose order management system. The various aspects discussed herein may be realized in isolation and/or in combination with one or more others of the aspects presented herein and thereby compose one or more additional aspects. In this application, the term aspect is used synonymous to the term embodiment. In other words, one or more features of one or more aspects and/or one or more features of one or more embodiments described in this application may be separated from the remaining features of the corresponding aspect and/or embodiment and combined with separated features of one or more aspects and/or embodiments to create new aspects and/or embodiments. In this regard, the aspects described herein may be used in the context of a work station of a medical dose management system as described above. In particular, the workstation may be adapted and suitable for the use in a system for medical dose preparation management. One aspect may relate to the use of a workstation for medical dose preparation management. Another aspect may relate to a medical dose management system and the workstation may be a component of the medical dose management system.

Accordingly, the work station may generally include an imaging device (e.g., digital camera) supported relative to a medication preparation staging region. The medical dose preparation staging region may be at least partially defined by a base having a length and a width. That is, the base may include a surface for supporting an object such as a medication receptacle used in the preparation of a medical dose order at the work station. The imaging device may have an imaging field encompassing at least a portion of the medication preparation staging region. The imaging device may be operable to capture digital image data (e.g., still digital images and/or video data stream) of the medical dose preparation staging region (e.g., including medication receptacles used in the medical dose order or prepared by the work station).

In this respect, one aspect may include an imaging device that is located at least partially within a housing. In turn, the imaging field of the imaging device may extend through an opening of the housing. Additionally, a transparent shield may be disposed between the imaging device and the medication preparation staging region. In particular, the transparent shield may cover at least a portion of the imaging device (e.g., corresponding to at least a lens of the imaging device). The transparent shield may extend across at least a portion of or substantially all of the opening through which the imaging field of the imaging device extends.

In the latter regard, the transparent shield and the housing may define an enclosed volume. As such, the transparent shield and the housing may define a continuous outer surface disposed about the enclosed volume. Thus, the imaging device may be disposed within the enclosed volume. As a result, the imaging device may be shielded from an environment external to the enclosed volume (e.g., the camera may be isolated from spills or other potential contact with liquids or hazardous substances such as may occur during dose preparation or during the cleaning of the work station).

In another aspect, an imaging device may be provided having at least one fixed optical setting. In an embodiment, the fixed optical setting may be preset (e.g., during the manufacture of the work station). The fixed optical setting may result in a depth of field that encompasses substantially the entire medical dose preparation staging region (e.g., such that an image of an object in the medical dose preparation staging region is disposed within the depth of field). In various embodiments, the at least one fixed optical setting may correspond to at least one of an aperture setting, a focus setting, a magnification setting, and/or other appropriate optical setting.

In another aspect, at least one light source (e.g., one or more LEDs) may be disposed in the housing. As such, the light source(s) may be operable to emit light from the housing in a direction toward the medication preparation staging region. As such, the light source may also be disposed in the enclosed volume such that the light source is also shielded from an environment external to the enclosed volume.

In still another aspect, light polarization filters may be employed in conjunction with a light source and an imaging device of the work station (e.g., to reduce glare in a medical dose preparation image captured by the imaging device). For example, the work station may include a first polarization filter disposed between the imaging device and the medication preparation staging region and a second polarization filter disposed between the light source and the medication preparation staging region. In an application, at least a portion of a transparent shield (e.g., as discussed above) may comprise at least one of the first or second polarization filters. In an embodiment the transparent shield may comprise both, the first and the second polarization filters. In an embodiment, the first polarization filter and the second polarization filter may collectively cover at least a portion of the opening of the housing. The first polarization filter and the second polarization filter may be disposed in non-overlapping relation, and the first polarization filter and the second polarization filter may have perpendicular polarization orientations. Accordingly, the polarization filters may work in conjunction to reduce glare from objects in the medication dose preparation staging region.

In an embodiment, the imaging device may be disposed in a central region of the housing opening and a peripheral region may extend about the central region. A plurality of light sources may be disposed in the peripheral region (e.g., spaced about the central region). In this regard, the first polarization filter may cover a portion of the opening corresponding to the lens of the camera and the second polarization filter may cover a portion of the opening corresponding to the light source(s).

In an embodiment, the peripheral region may extend in at least a first direction corresponding to the width of the base. The peripheral region may also extend in at least a second direction corresponding to one of the length of the base or a height of the medical dose preparation staging region extending from the base. For example, as described in greater detail below, the imaging device may be disposed in a plurality of positions relative to the medical dose preparation imaging device. Accordingly, depending upon the orientation of the imaging device, the peripheral region may extend in a direction corresponding to the length of the base and when in a second position, the peripheral region may extend in a direction corresponding to the height of the medical dose preparation staging region (e.g., extending normal to the base).

In this regard, a support member may extend between the base and the housing for supportably disposing the imaging device relative to the base (e.g., between a plurality of different positions of the imaging device relative to the base). That is, the support member may be selectively positionable in at least a first position and a second position relative to the medication preparation staging region of the base. The support member may be moveable between the first position and the second position. Additionally or alternatively, the support member may be selectively positionable in a plurality of different positions relative to the medication preparation staging region.

In an embodiment, the support member may include a first portion attached to the base and a second portion attached to the imaging device. The second portion may be moveable relative to the first portion between the first position and the second position. For instance, the first portion may be hingedly connected to the second portion. Accordingly, the first portion and the second portion may be pivotally disposable between the first position and the second position. In an embodiment, movement between the first position and the second position may be dampened.

When the support member is in the first position, the imaging field of the imaging device may extend between the imaging device and the base to encompass at least a portion of the medical dose preparation staging region. When the support member is in a second position, the imaging field may extend in a direction parallel to a support surface of the base to encompass at least a portion of the medical dose preparation staging region.

In one embodiment, the support member may extend from the base adjacent to an edge of the base extending along the width. The work station may be disposed in a laminar flow hood or the like. Accordingly, a flow of air from the laminar flow hood may be parallel to a direction corresponding to the width of the base. That is, the support may be positioned relative to the base so as not to obstruct the laminar flow of air across the base (e.g., substantially the entire base may be exposed to laminar air flow).

Furthermore, it is recognized that elimination and/or reduction of the number of wires, cables, and the like from the work station may be advantageous. For example, the reduction of wires and/or cables may provide fewer structures and surfaces that require cleaning. Furthermore, in the case where a containment structure such as a laminar airflow hood, isolator, or biological safety cabinet is used, the routing of cables to an exterior environment of the containment structure may present difficulties in maintaining an appropriate containment level of the containment structure. As such, the reduction and/or elimination of wires, cables, and the like at the work station may improve the ability to clean the work station and may assist in maintaining a level of containment of a containment structure employed at the work station.

In this regard, in an aspect, an umbilical may be provided that is at least partially disposed within a support member (e.g., to reduce the number of cables, wires, or the like in the work station). The umbilical may include at least one of a signal communication member and a power communication member. That is, the umbilical may consolidate a number of conductive members into a single cable to reduce the number of cables that need to be provided. The umbilical may be in operative communication with a processor.

In another embodiment, wireless technology may be incorporated at the work station (e.g., to completely eliminate the need for wires and the like). That is, technology may be incorporated into the work station to wirelessly communicate signals between the various components and the processor. For example, image data, lighting control data, scale information, or other communication between the devices of the work station and a processor may be facilitated by way of wireless communication. Additionally, a battery may be provided with the camera stand to facilitate wireless operation. For example, the battery may be replaceable or rechargeable to facilitate continued wireless operation.

In an application, the base of the work station may be supportably engageable with a surface with one or more suction cups. In this regard, the camera stand may be securely retained on a surface. Furthermore, the suction cups may provide some measure of vibration isolation from an exterior environment.

In another aspect, a support platform may be provided that is removably disposable relative to the base. The removal of the support platform may facilitate cleaning of the support platform. The support platform may at least partially define the medication preparation staging region. The support platform may be made of a UV resistant material to withstand discoloration or deterioration of the support platform.

In an aspect, a support surface of the support platform may define a plurality of medication receptacle engagement features. Accordingly, the support platform may include a reference plane corresponding to a surface of the support surface. In this regard, the support surface may include at least one groove defined in the support surface that may extend from the reference plane by a first depth. Additionally, the support surface may include at least one channel defined in the support surface that may extend from the reference plane by a second depth. The groove and the channel may be operable to engage a medication receptacle disposed in the medication preparation staging region. In an embodiment, the first depth may be less than the second depth.

Also, in one implementation, the groove may include a first concave surface extending from the reference plane to the first depth. The channel may comprise a second concave surface extending from the reference plane to the second depth. The first concave surface may have a first radius of curvature greater than a second radius of curvature of the second concave surface. In an embodiment, the support surface may include a plurality of grooves and/or a plurality of channels. At least one of said plurality of grooves may be disposed perpendicular to at least one of the channels. Furthermore, at least one of the plurality of grooves may extend in a first direction of the base corresponding to a width of the support surface. For example, at least one groove may extend across substantially all of the support surface in a first direction corresponding to the width of the support surface. Also, at least one of the plurality of channels may extend in a second direction of the base corresponding to the length of the support surface. For example, at least one channel may extend across substantially all of the support surface in a second direction corresponding to a length of the support surface.

Still another aspect may include a mechanism for alerting a user to the fact that a medical dose preparation image has been captured. For example, a user control device (e.g., a foot switch) may be provided that is in operative communication with the processor to initiate a capture of a medical dose preparation image from the image data obtained by the image device in response to a user input received at the user control device. In other words, the user control device may be operable to and/or adapted to receive a user input for receiving a user input to initiate capture of a medical dose preparation image from a video data stream output by the imaging device. Alternatively or additionally, other methods of triggering capture of a medical dose preparation image may be provided without limitation. In any regard, upon capture of a medical dose preparation image, an intensity of a light source may be automatically modified from a default intensity of light emitted to a modified intensity of light. In other words the light source may be operable and/or adapted such that an intensity of the at least one light source is automatically modified from a default intensity of light emitted to a modified intensity of light emitted. The change in light intensity may occur at a first predetermined period after the capture of the medical dose preparation image. Furthermore, the light source may be automatically returned from the modified intensity of light to the default intensity of light at a second predetermined period after the first predetermined period. In other words, the light source may operable to and/or adapted to be automatically returned from the modified intensity of light to the default intensity of light at a second predetermined period after the first predetermined period. The light source may be automatically returnable from the modified intensity of light to the default intensity of light. In this regard, the light source may be controlled to "blink" or "flicker" to indicate to a user that the image has been captured so that the user may proceed in the workflow.

In an embodiment, a scale may be provided that is in operative communication with the processor. The scale may be operable to output a weight corresponding to a medication receptacle that is supportably disposed in the medication preparation staging region. In this regard, the scale may be provided in corresponding relation to the base (e.g., disposed relative to the base and/or integrated with the base).

For example, the scale may be generally used to perform a gravimetric analysis of an item disposed in the medical dose preparation staging region. For example, upon capture of a medical dose preparation image, the weight of the medication receptacle may be recorded by the processor from the scale at substantially the same time that the medical dose preparation image is captured. In other words, the processor may be operable to and/or adapted to—upon receipt of a user input—record the weight from the scale at substantially the same time that the medical dose preparation image is captured. In this regard, the work station may also include a memory in operative communication with the processor for storing the weight and the medical dose preparation image. For example, the weight and the medical dose preparation image may be associatively stored in the memory. As such, the processor may be operable to compare the measured weight of the medication receptacle to an anticipated weight of the medication receptacle (e.g., provided in metadata of the order). In this regard, the processor may be operable to calculate a deviation of the measured weight to the anticipated weight. The deviation may be associatively stored in the memory with the weight, the medical dose preparation image, and/or the dose order. Furthermore, the deviation may be compared to a threshold deviation value. Accordingly, when the deviation exceeds a threshold deviation, an alert may be provided to a user. In this aspect, the base, the imaging device, and the scale may be interconnected for movement as a single unit. Moreover, the processor may be operable to and/or adapted to compare the deviation to the threshold deviation, and provide the alert to the user.

Another aspect may relate to a method comprising the steps of outputting of a video data stream of the imaging field, receiving the video data stream of the imaging field, initiating a capture of a medical dose preparation image from the video data stream in response to a user input received at a user control device, and outputting a weight corresponding to a medication receptacle that is supportably disposed in a medication preparation staging region. The method may further provide for upon receipt of the user input, recording of the weight at substantially the same time as the capture of the medical dose preparation image.

Numerous additional features and advantages of the present invention will become apparent to those skilled in the art upon consideration of the embodiment descriptions provided hereinbelow.

DETAILED DESCRIPTION

Figure 1:
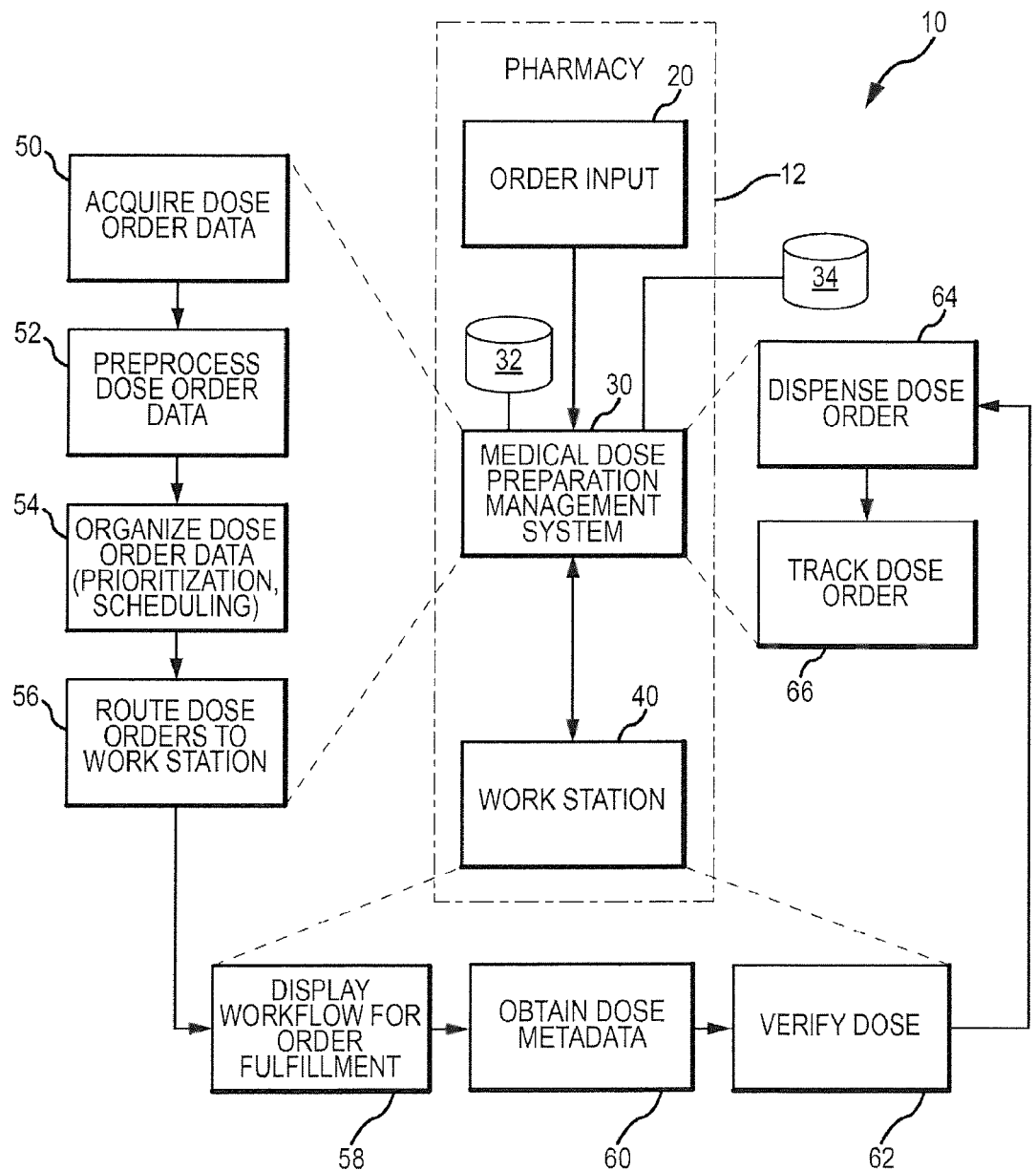
FIG. 1 is a schematic and flow chart depicting an embodiment of a medical dose preparation management system and an embodiment of the operation thereof.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 shows an embodiment of a system 10 that may be used at a care provider pharmacy 12 to assist in the preparation and/or management of medical doses. The system 10 may include a dose order input 20 to receive medical dose orders. The dose order input 20 may be utilized by care provider personnel (e.g., physicians, nurses, etc.) to order medical doses.

The medical dose orders received at the dose order input 20 may be specific to patients or may be orders that are not associated with a patient at the time of ordering. In this regard, the medical dose order may correspond to a contained medication unit that may comprise one of the following:

a patient specific unit comprising a medication unit designated for administration to a specific patient;

a non-patient specific unit comprising a medication unit to be subsequently designated for administration to a specific patient; or, a medication component source unit to be used in the preparation of a patient specific unit or a non-patient specific unit (e.g., that will be designated for administration to a specific patient after preparation).

Examples of contained medication units that may correspond to medication dose orders include:

compounded sterile products;

injectable medications;

chemotherapy preparations; or nutritional supplements requiring administration by a patient care provider (e.g., sterile injectable nutritional supplements).

In the latter regard, nutritional supplements may include total parenteral nutrition (TPN) or components of TPN. Furthermore, nutritional supplements may include partial nutritional supplements. The nutritional supplements may include a pre-mix bag, base and additive components separately or in combination, or other forms of nutritional supplements or components thereof. The nutritional supplements may be for administration via intravenous injections, in an edible form, or for use with a feeding tube or the like.

In any regard, the medical dose may include one or more portions of information that may be used to assist in preparation of the mediation dose, may be associated with the administration of the dose order to a patient, or may otherwise relate to the dose order. For example, the dose order may include information corresponding to:

a medication identity;

a medication amount;

a medication concentration;

information associated with a patient to whom the medication unit associated with the medication dose order is to be administered;

scheduling information (e.g., an administration time) for the medication unit associated with medication dose order; or other appropriate information regarding the medication unit associated with the medication dose order.

In any regard, the medical dose orders may be communicated to a medical dose preparation management system 30. The medical dose preparation management system 30 may be operable to acquire 50 dose order data from the dose order information received from the order processor 20. The medical dose preparation management system 30 may also preprocess 52 dose order data. The preprocessing 52 may include, for example, generating a digital dose order record that is maintained by the medical dose preparation management system 30. The digital dose order record may be automatically populated with data that may be obtained from the order such as, for example, any of the information described above in connection with the medical dose order. In this regard, information may be parsed, scraped, or otherwise obtained from the medication dose order received at the order input 20. Specifically, in an embodiment, the medical dose preparation management system 30 may be operable to scrape data addressed to a human readable output (e.g., a printer) from the order input 20 to populate the medical dose order record with data corresponding to the medical dose order.

In an embodiment, the medical dose preparation management system 30 may be in operative communication with a mediation dose order database 32. In this regard, the medication dose order database 32 may be located at the care provider facility (i.e., be on-site relative to the care provider hospital 12). The medical dose preparation management system 30 may additionally or alternatively be operable to communicate with a remote medication dose order database 34. In this regard, the medical dose preparation management system 30 may communicate with the remote medication dose order database 34 via a network or the like. In either regard, the medication dose order database 32 or 34 may be operable to store medication dose order records in the medication dose order database 32 and/or 34. In addition, the medication dose order database 32 or 34 may store dose order metadata in corresponding relation to respective ones of the stored medication dose orders. The medication dose order database 32 or 34 may store active dose orders (e.g., corresponding to dose orders that have been generated but not yet administered to the patient) or archived dose orders (e.g., corresponding to dose orders that have been administered to a patient). Redundant data may be stored at the on-site medical dose order database 32 and the off-site medical dose order database 34. For example, the off-site medical dose order database 34 may be a backup version of the on-site medical dose order database 32.

In any regard, medical dose order metadata may be stored in corresponding relation to a medication dose order. The medical dose order metadata may include, for example, the following types of data:

medication source data indicative of at least one of:

a manufacturer of a component of the contained medication unit corresponding to the medication dose order, a lot number of a component of the contained medication unit corresponding to the medication dose order, an expiration date of a component of the contained medication unit corresponding to the medication dose order, a serial number of a component of the contained medication unit corresponding to the medication dose order, or a drug code indicative of the identity of a component of the contained medication unit corresponding to the medication dose order;

chain of custody data indicative of at least one of:

a listing of entities in possession of a component of the contained medication unit corresponding to the medication dose order or the contained medication unit corresponding to the medication dose order, a listing of users that have taken an action with respect to the contained medication unit corresponding to the medication dose order, wherein the listing of users is correlated to specific actions taken by each user, or tracking information corresponding to physical movement of a component of the contained medication unit corresponding to the medication dose order or the contained medication unit corresponding to the medication dose order;

fulfillment data indicative of at least one of:

image data corresponding with a component of the contained medication unit corresponding to the medication dose order or the contained medication unit corresponding to the medication dose order, scanned data obtained from a component of the contained medication unit corresponding to the medication dose order, analytic data regarding a component of the contained medication unit corresponding to the medication dose order or the contained medication unit corresponding to the medication dose order, pharmacist review data corresponding with at least one pharmacist review of a component of the contained medication unit corresponding to the medication dose order or the contained medication unit corresponding to the medication dose order, compliance data corresponding with best practices associated with a component of the contained medication unit corresponding to the medication dose order or the contained medication unit corresponding to the medication dose order, sterility assessment data corresponding to a component of the contained medication unit corresponding to the medication dose order or the contained medication unit corresponding to the medication dose order, a listing of actions corresponding to a component of the contained medication unit corresponding to the medication dose order or the contained medication unit corresponding to the medication dose order, time stamp data corresponding to actions corresponding to a component of the contained medication unit corresponding to the medication dose order or the contained medication unit corresponding to the medication dose order, a listing of life cycle events taken with respect a component of the contained medication unit corresponding to the medication dose order or the contained medication unit corresponding to the medication dose order weight data corresponding to a measured and/or anticipated weight of a component of the contained medication unit corresponding to the medication dose order or the contained medication unit corresponding to the medication dose order; or environmental data indicative of at least one of:

a temperature to which a component of the contained medication unit corresponding to the medication dose order or the contained medication unit corresponding to the medication dose order has been exposed, a temperature to which and corresponding time period for which a component of the contained medication unit corresponding to the medication dose order or the contained medication unit corresponding to the medication dose order has been exposed, whether a component of the contained medication unit corresponding to the medication dose order or the contained medication unit corresponding to the medication dose order is refrigerated, whether a component of the contained medication unit corresponding to the medication dose order or the contained medication unit corresponding to the medication dose order is frozen, a temperature profile experienced by a component of the contained medication unit corresponding to the medication dose order or the contained medication unit corresponding to the medication dose order, or accelerometer data corresponding to forces experienced by a component of the contained medication unit corresponding to the medication dose order or the contained medication unit corresponding to the medication dose order.

As may be appreciated from the foregoing description of the medical dose order metadata, a medical dose order may inherit metadata from components used in the preparation of the medical dose order. In a simple example, a medical dose order may include a first component (e.g., a drug) to be mixed with a second component (e.g., a diluent). The first component may have one or more portions of metadata as described above that are associated with the first component. Additionally, the second component may have one or more portions of metadata as described above that are associated with the second component. Thus, a medical dose order that is prepared using the first component and the second component may inherit the metadata from each of the first component and second component. In this regard, a plurality of generations of metadata may be compiled and attributed for a given medical dose order. In an embodiment, metadata for any and all components used to prepare the dose order may be compiled and attributed for a given medical dose order. As such, metadata information for the medical dose order may include metadata originating with source components provided by a manufacturer of the components of a dose order.

The medical dose preparation management system 30 may also be operative to organize 54 dose orders. The organization 54 may include prioritization, scheduling, or other tasks associated with the organization or management of dose orders. The medical dose preparation management system 30 may also be operative to route 56 dose orders to an appropriate work station 40 for use in fulfillment of the dose order. In this regard, a plurality of work stations 40 may be provided in communication with the medical dose preparation management system 30. Different ones of the plurality of work stations 40 may each be suited for different operations related to medical dose order management. As such, depending on the nature of a medical dose, a particular type of work station 40 may be used to prepare the dose. The work station 40 may be on-site relative to the care provider hospital 12 as depicted in FIG. 1 or may be off-site. In this regard, the routing 56 may include communications over a network to a remote work station 40. Furthermore, the system 10 may include a combination of on-site work stations 40 as well as off-site work stations 40 to which dose orders may be routed 56.

In any regard, the medical dose preparation management system 30 may be in operative communication with one or more work stations 40. The routing 56 of dose orders may be at least partially based on one or more factors related to the dose order or the preparation of the dose order. For example, as stated above, the nature of the contained medication unit corresponding to the dose order (e.g., whether a dose order is a chemotherapy dose order, a parenteral dose order, or other specialized dose order) may factor into a determination regarding the routing 56 of the dose order. Additionally or alternatively, the capabilities of the various work stations 40 in relation to the manner in which the dose order is to be prepared may be considered. For example, some orders may require different levels of containment, hooding, or other precautions that may or may not be provided at each work station 40. In an embodiment, other parameters such as technician schedules, work station schedules, work station location, medication dose order scheduling information, or other information may be used alone or in combination to route 56 dose orders to a particular work station 40.

At the work station 40, a work flow corresponding to the preparation of the medical dose order may be displayed 58. In this regard, a work flow that is specific to the medical dose order currently being prepared at the work station 40 may be presented to a technician at the work station 40 to assist or provide guidance to the technician preparing the dose order. Accordingly, the technician may follow a sequence of steps to prepare the medical dose based on the work flow displayed 58 that relates to the dose order.

During and/or after the preparation of the dose order, the work station 40 may be used to assist in obtaining 60 dose order metadata related to the medical dose order. For example, the work station 40 may allow for recording of documentation regarding the preparation of the medical dose such as, for example, acquiring barcode scans of products, capturing medical dose preparation images of medical dose order receptacles during or after use in the preparation of the dose, or obtaining other information related to the preparation of the dose. In an embodiment, one or more of the types of data described above in relation to the medication dose metadata may be acquired in connection with the preparation of the medical dose order at the work station 40.

At least a portion of the dose metadata obtained 60 regarding the medication dose may be stored for viewing by appropriate personnel (e.g., a pharmacist). In this regard, the dose metadata may be utilized to verify 62 the prepared dose prior to the dose being dispensed from the pharmacy 12. In an embodiment, the metadata collected at the work station 40 may be made available to a pharmacist via a network. In this regard, a pharmacist tasked with verifying 62 a dose order may access the information and/or data remotely (e.g., in a location in the hospital but outside the IV room or even entirely remove from hospital premises via the network). The ability to remotely access the metadata may allow the pharmacist to avoid having to enter the IV room to verify 62 a dose order (i.e., thus avoid the potentially burdensome gowning procedures commonly associated with entering the controlled environment of an IV room). The verifying 62 may include inspection of medical dose preparation images, obtained information, or other data regarding the medical dose order by the pharmacist. For example, the pharmacist may verify the correct medication was prepared in the correct manner and/or in the correct amounts based on metadata gathered and stored during the preparation of the medical dose order. If the medication dose order is incorrect in any regard, the pharmacist may request the medication dose order be reworked or restarted.

Once the dose order has been prepared and verified 62, the medical dose preparation management system 30 may dispense 64 the dose order. When dispensing 64 the dose order, the dose order may be dispatched from the pharmacy 12 for administration to a patient by the care provider. For example, the dose may be administered at the care provider hospital 12 or an offsite location under the direction or supervision of the care provider.

The medical dose preparation management system 30 may also facilitate tracking 66 of the dose order to administration to the patient. The pharmacy work flow manager 30 may also retain records associated with each dose that may be stored or archived. For example, the records may be stored digitally in electronically indexed and searchable form. The records may include at least a portion and preferably all metadata regarding each dose.

Figure 2:
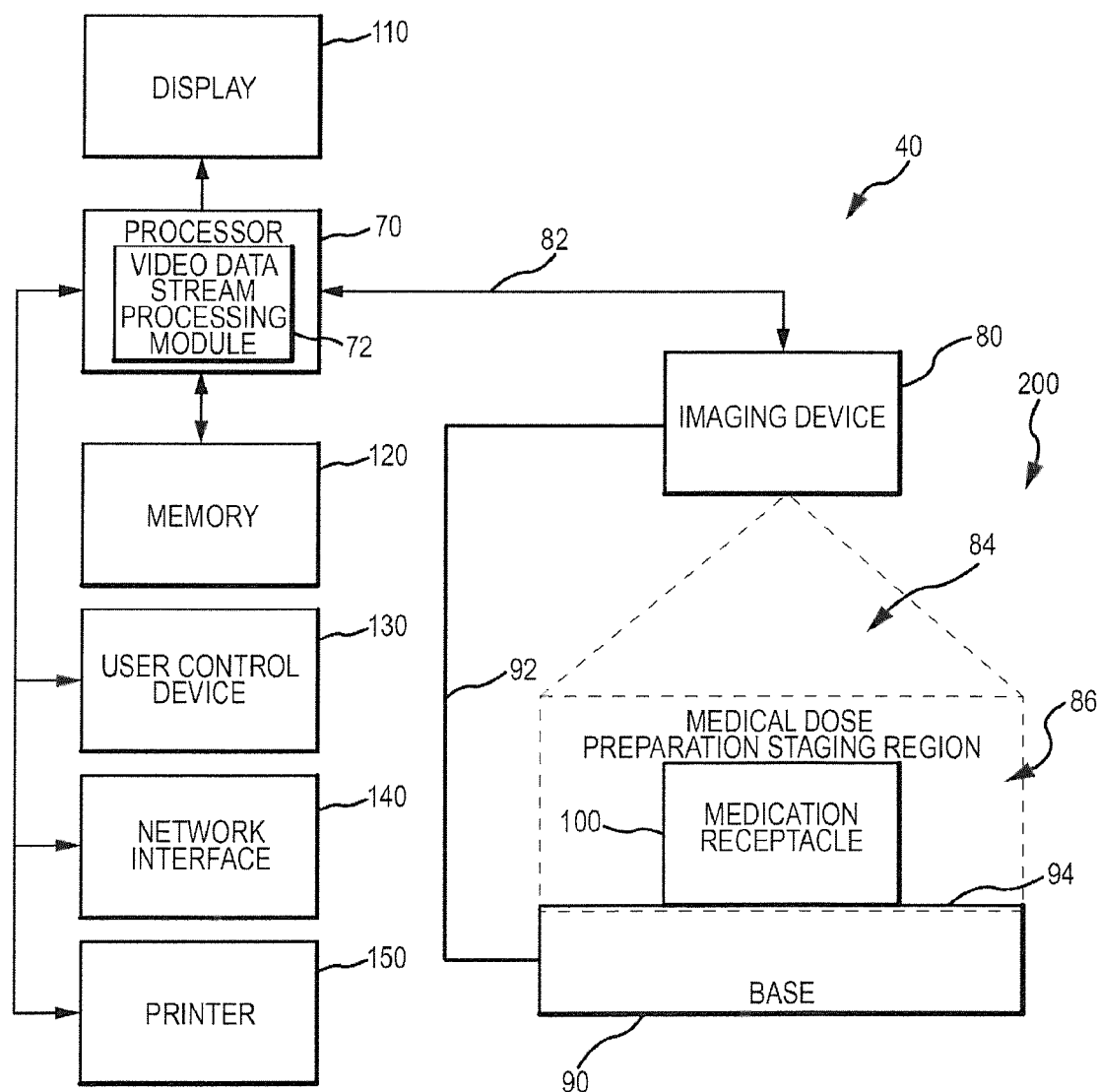
FIG. 2 is a schematic view of an embodiment of a work station for use in a medical dose preparation management system.

With further reference to FIG. 2, a schematic view depicting an embodiment of a work station 40 is shown. The work station 40 may include a processor 70 in operative communication with an imaging device 80. The imaging device 80 may be a digital camera operable to output digital image data. The digital image data may comprise still images and/or digital video. In this regard, the imaging device 80 may output a video data stream 82 that is received by the processor 70. In this regard, the processor 70 may include a video data stream processing module 72 for processing the video data stream 82 received at the processor 70 from imaging device 80. While the various components shown in FIG. 2 are shown in direct communication, the various components may also be in operative communication by way of a network interface or the like.

The imaging device 80 may include an imaging field 84. The imaging field 84 may encompass a medical dose preparation staging region 86. The imaging device 80 may be supportably mounted to a base 90. For example, a support 92 may extend from the base 90 to the imaging device 80 to support imaging device 80 relative to the base 80. In this regard, in an embodiment the medical dose preparation staging region 86 may include a support surface 94 of the base 90. The medical dose preparation staging region 86 may also include a volume above the surface 94 (e.g., extending from the surface in a direction normal to the surface and/or toward the imaging device 80). In any regard, the imaging field 84 of the imaging device 80 may encompass the medical dose preparation staging region 86 that may supportably receive a medication receptacle 100. In turn, the imaging device 80, support 92, and base 90 may collectively define a camera stand 200. As such, the camera stand 200 may be used at a work station 40 to support the imaging device 80 relative to the base 90 to obtain medical dose preparation image and/or other metadata during the preparation of the medical dose order.

The medication receptacle 100 supportable by the base 90 in the medical dose preparation staging region 86 may include any material, container, apparatus, or other object that is used in the preparation of a dose. For example, the medication receptacle 100 may be or include a source receptacle, a transference receptacle, or an administration receptacle. A source receptacle may store a medication product as stored in the pharmacy prior to compounding or dose preparation. In this regard, the source receptacle may be a receptacle as packaged by and received from a drug manufacturer. As such, the source receptacle may include information thereon relating to the medication. For example, the product name, concentration, amount, lot information, expiration information, a serial number, other manufacturing information or other information may be associated with the medication and/or may appear on the source receptacle. The medical dose preparation management system 30 may be operable to store metadata regarding the source receptacle including any of the foregoing portions of data that may appear on the source receptacle. In this regard, the source receptacle may be identifiable by the work station 40 (e.g., via the use of a machine readable indicium such as a bar code or the like).

Furthermore, the medical dose preparation management system 30 may be operable to attribute metadata from the source receptacle to the dose order in which the source receptacle is used as described above. The source receptacle metadata may even be attributed to or appended to the metadata for the medical dose order when the source receptacle comprises a pre-prepared medication that has been compounded at the pharmacy and disposed in the source receptacle for later use in the preparation of a dose. In this regard, the metadata for several generations of components used to prepare a medical dose order (e.g., originating from original source components received from a manufacturer such as a drug manufacturer) may be attributed to the medical dose order. As such, the medical dose order metadata may include information regarding all components used in the medical dose order including inherited metadata. The metadata for the various components may be retrieved upon identification of the receptacle 100 at the work station 40 (e.g., by way of scanning a machine readable indicium). In various embodiments, the source receptacle may include a vial, a syringe, a bottle, a bag, or other appropriate medication receptacle known in the art.

An administration receptacle may be any receptacle used during the administration of the medical dose to the patient. The administration receptacle may contain any medication, diluent, supplement, or any other material to be administered to the patient. In various embodiments, the administration receptacle may include a syringe, an IV bag, or other appropriate medication receptacle used in the administration of a substance to patient. An administration receptacle may also include metadata that is included in the metadata for the prepared medical dose order.

The transference receptacle may be used to transfer a substance from a source receptacle to the administration receptacle. For example, the transference receptacle may be a syringe or any other appropriate receptacle known in the art capable of transferring a substance from the source receptacle to the administration receptacle. A transference receptacle may also include metadata that is included in the metadata for the prepared medical dose order.

Returning to FIG. 2, the processor 70 may be in further operative communication with a display 110. In this regard, the video data stream 82 received from the imaging device 80 may be displayed on the display 110 in a manner that is perceivable by user. The video data stream 82 displayed on the display 110 may be processed by way of the video data stream processing module 72. For example, the video data stream processing module 72 may be operable to capture still images from the video data stream 82. The video data stream 82 may include a series of images displayed at a given frame rate. For example, the frame rate may be 5-10 frames/second.

Medical dose preparation images captured by the video data stream processing module 72 may include one or more medication receptacles 100 used in the course of preparing a medical dose order. In this regard, the preparation of medical dose orders may be documented by capturing images of the medication receptacles 100 used to prepare the dose. The medical dose preparation images may be stored as metadata regarding the medical dose order. A medical dose preparation image may include one or more medication receptacles at various stages during the preparation of the dose. For example, a source receptacle, a transference receptacle, or an administration receptacle may be imaged before, during or after preparation of the dose.

The medical dose preparation images captured by the video data stream processing module 72 may be stored in a memory 120 in operative communication with the processor 70. In this regard, the medical dose preparation images may be stored locally in the memory 120 at the work station 40. Additionally or alternatively, the medical dose preparation images may be communicated to a remote location (e.g., an on-site medication dose order database 32 or an off-site medication dose order database 34 shown in FIG. 1) by way of a network interface 140 in operative communication with the processor 70. In any regard, medical dose preparation images may be accessible such that images may be later reviewed in the course of verifying (e.g., the verifying 62 described above in relation to FIG. 1) the medical dose order and/or for maintaining records regarding the dose orders prepared by the work station 40 and/or the hospital pharmacy 12 generally.

The processor 70 may also be in operative communication with a user control device 130. The user control device 130 may be operable to receive an input from a user (e.g., a pharmacy technician preparing a dose). The user control device 130 may be, for example, a foot pedal, a button, a touch screen, a mouse, a keyboard, or other user input device known in the art. A user may utilize the user control device 130 to trigger the capture of a medical dose preparation image from the video data stream 82. For example, a medication receptacle 100 may be viewed by the user by observing the display 110 displaying the video data stream 82 captured by the imaging device 80 of imaging field 86 including the medication receptacle 100. Once the image displayed on the display 110 is acceptable to the user, the user may use the user control device 130 to trigger the capture of the medical dose preparation image for storage in the memory 120 or in a remote database as described above.

The work station 40 may also include a printer 150 that is operative to print dose labels associated with a medical product, a dose that is in progress, and/or a completed dose. In this regard, the printer 150 may be a label printer operative to print labels used in the pharmacy 12 and/or hospital in connection with metal doses and/or medical dose orders.

Figure 3:
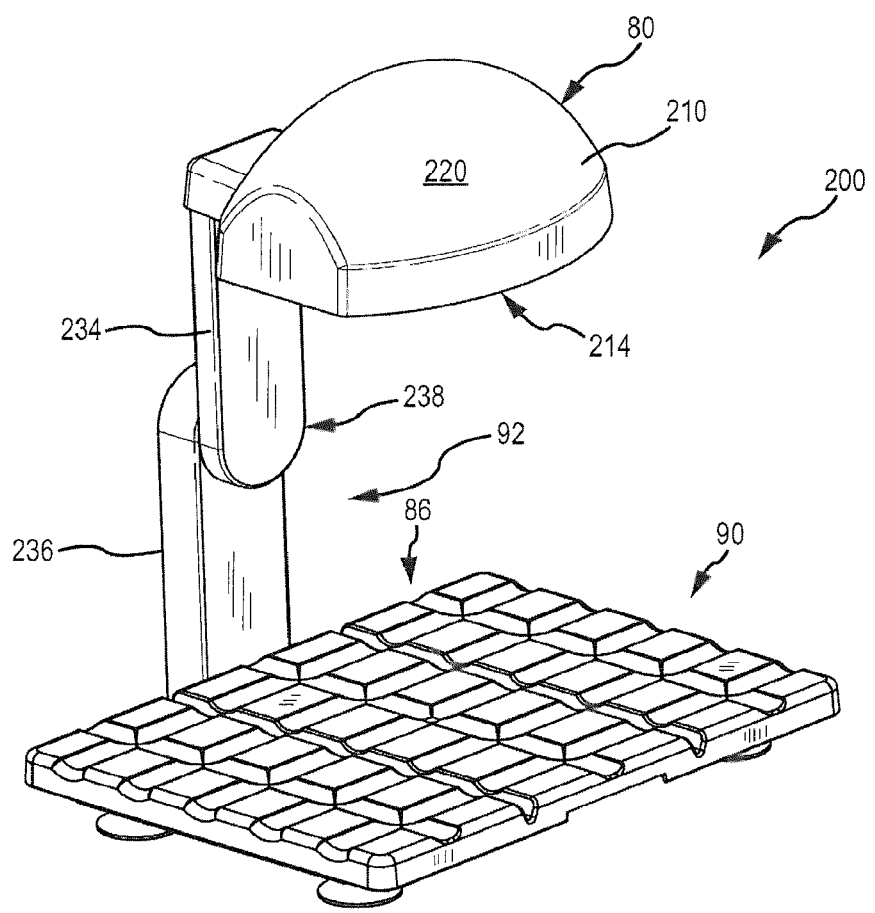
FIG. 3 is a perspective view of an embodiment of a camera stand of a work station.
Figure 4:
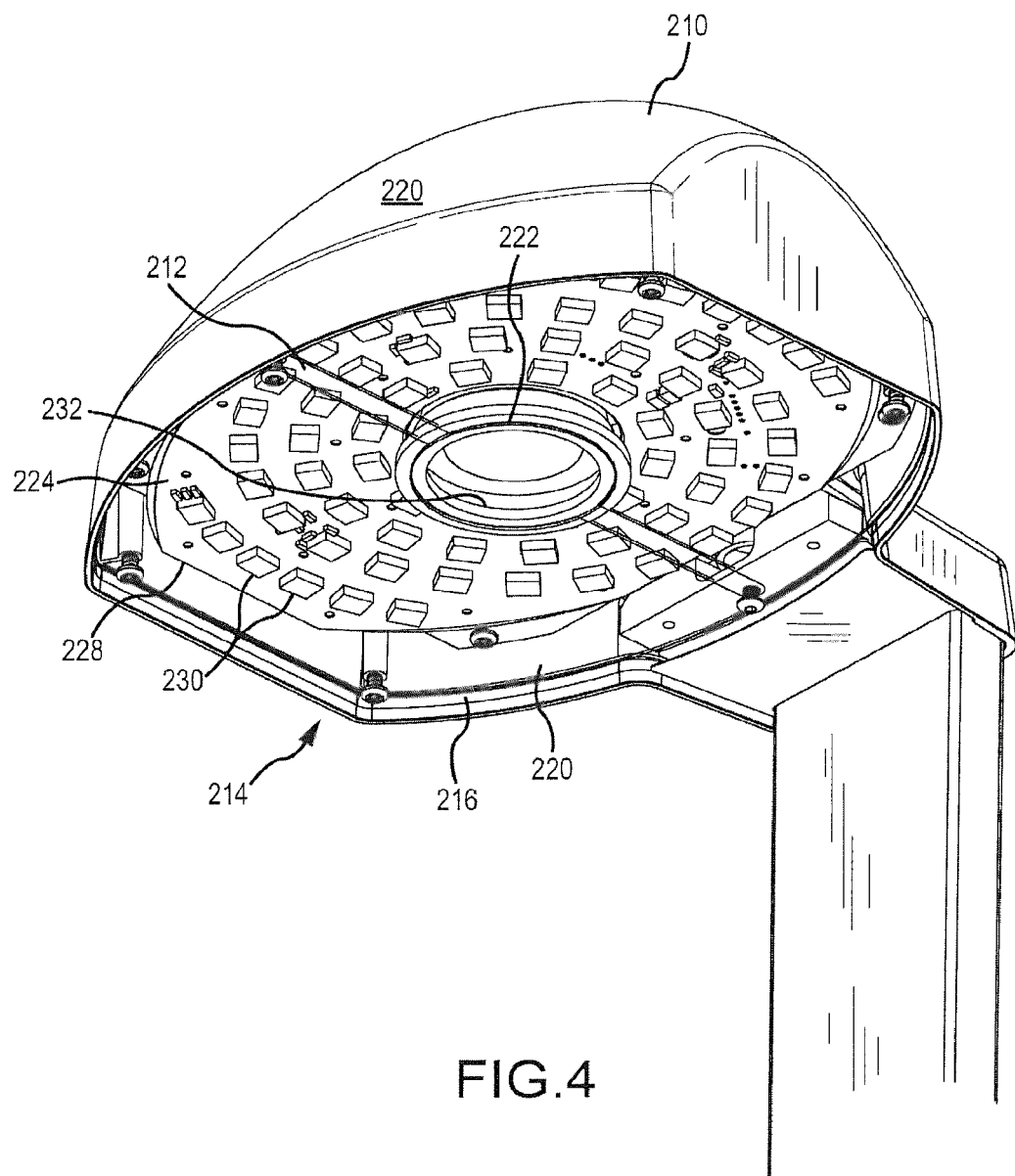
FIG. 4 is a perspective view of an embodiment of a housing of the camera stand of FIG. 3.
Figure 5:
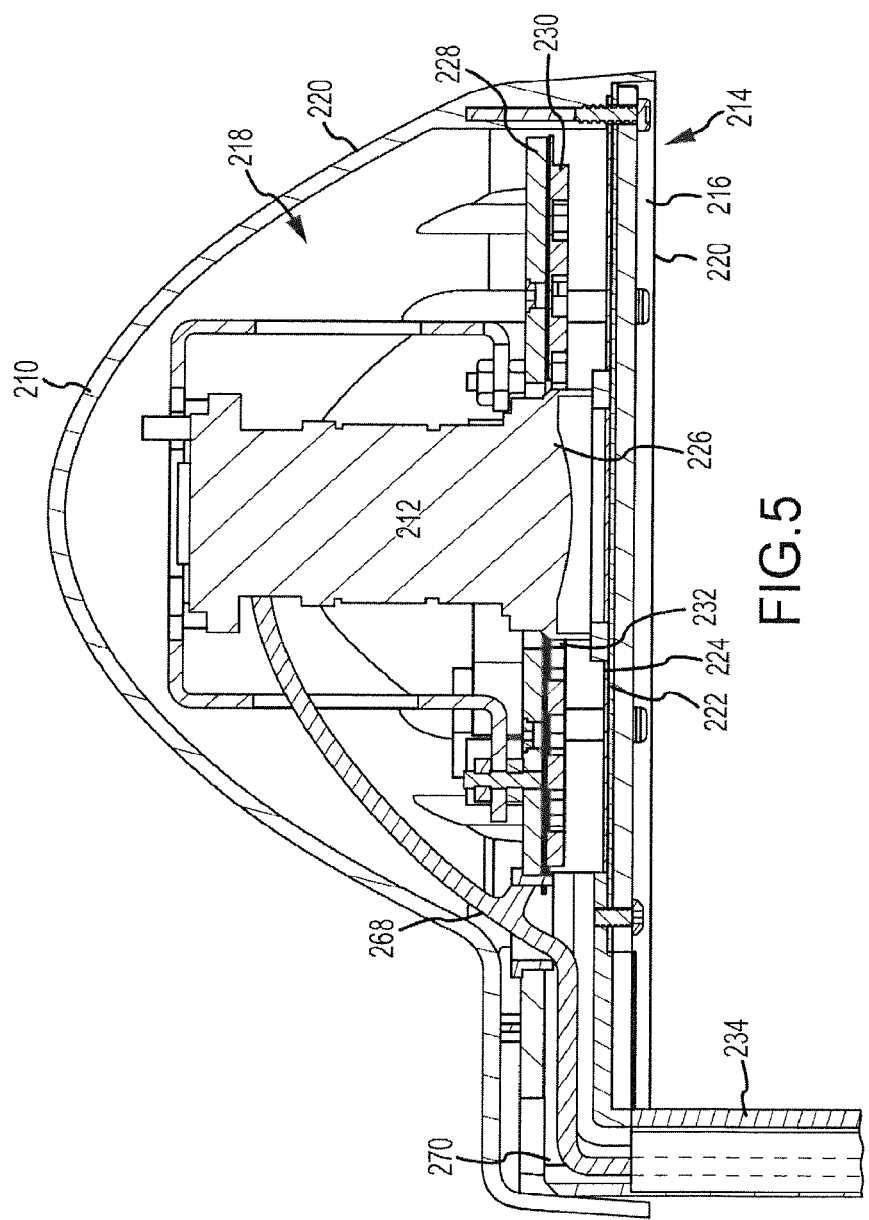
FIG. 5 is a cross-sectional view of the embodiment of the housing of the camera stand of FIG. 3 showing a camera and light sources disposed in an enclosed volume of the housing.

With further reference to FIG. 3, an embodiment of a camera stand 200 is depicted. As described above, the camera stand 200 may include an imaging device 80, a support 92, and a base 90. With respect to the imaging device 80, an imaging device housing 210 may contain a camera 212 (as shown in FIG. 5). With additional reference to FIGS. 4 and 5, the housing 210 may define an opening 214. The opening 214 may be disposed relative to the housing 210 such that the camera 212 may be directed through the opening 214 toward the medical dose preparation staging region 86. A transparent shield 216 may be disposed within the opening 214. For example, the transparent shield 216 may be secured to the housing 210.

The transparent shield 216 may extend across at least a portion of the opening 214 (e.g., in corresponding relation to the lens 226). In an embodiment, the transparent shield 216 may extend across substantially the entire opening 214. In this regard, the housing 210 and the transparent shield 216 may collectively define an enclosed volume 218 (best seen in FIG. 5) in which the camera 212 may be disposed. In this regard, the transparent shield 216 and housing 210 may also define a continuous outer surface 220 that extends about the enclosed volume 218. Accordingly, the continuous outer surface 220 may allow for easy cleaning of the housing 210 and the transparent shield 216. For example, the continuous outer surface 220 may be wipeable by an operator to facilitate cleaning. As the continuous outer surface 220 may be resistant to fluids penetrating the enclosed volume 218, the components disposed within the enclosed volume 218 may remain dry when the outer surface 220 is exposed to fluids (e.g., cleaning products). Further aspects of the camera stand 200 discussed below may also assist in the cleaning of a work station 40.

Also disposed within the enclosed volume 218 may be a light source board 228. The light source board 228 may include one or more light sources 230 connected to the light source board 228. The light sources 230 may comprise individual light emitting diodes (LED). The light sources 230 may be attached to the light source board 228 such that power and/or control signals used in the operation of the light sources 230 are provided to the light sources 230 by way of the light source board 228. In this regard, the light source board 228 may provide a physical mounting substrate for supportably engaging the light sources 230 as well as providing electrical communication between the light sources 230 and the light source board 228. In this regard, the light source board 228 may be a printed circuit board (PCB) including attachment locations and appropriate electrical communication paths (e.g., conductive traces) to facilitate attachment and electrical communication between the light sources 230 and the light source board 228.

The light source board 228 may include an aperture 232. A lens 226 of the camera 212 may be aligned with the aperture 232 such that an imaging field 84 of the camera 212 defined by the lens 226 extends through the aperture 232. The aperture 232 may also be aligned with a central region of the opening 214 of the housing 210. As such, a peripheral region extending about the central region of the opening 214 may be occupied by the light source board 228, and thus the light sources 230. In this regard, the light sources 230 may be provided peripherally about the aperture 232 of the light source board 228, and thus the lens 226 of the camera 212. The light sources 230 may emit light through the opening 214. As such, the light emitted from the light sources 230 may at least partially coincide with the imaging field 84 of the camera 212. In this regard, the distribution of the light sources 230 as shown in FIG. 4 where the light sources 230 are distributed through the peripheral region of the opening 214 about the lens 226 and aperture 232 may facilitate the relatively uniform distribution of light from the light sources 230.

With further reference to FIG. 5, the camera 212 may be contained in the enclosed volume 218 defined by the housing 210 and the transparent shield 216.

As can further be appreciated in FIG. 5, one or more polarization filters 222 and 224 may be provided. As depicted, a peripheral polarization filter 222 and a central polarization filter 224 may be provided. At least a portion of the peripheral polarization filter 222 and at least a portion of the central polarization filter 224 may be disposed in non-overlapping relation. For example, the peripheral polarization filter 222 may be disposed in the peripheral region of the opening 214 in corresponding relation to the light source board 228 and the light sources 230. The central polarization filter 224 may be disposed in the central region of the opening 214 in corresponding relation to the lens 226 of the camera 212.

In this regard, the peripheral polarization filter 222 and the central polarization filter 224 may be disposed such that the direction of polarization of the filters are oriented perpendicularly to each other.

Accordingly, as light is emitted from the light sources 230, the emitted light may pass through the peripheral polarization filter 222 and, thus, be polarized according to the first direction of polarization associated with the peripheral polarization filter 222. The light may then travel toward the medical dose preparation staging region 86, which may become illuminated by the emitted light polarized in the first direction. The emitted light originating from the light sources 230 may be reflected from the medical dose preparation staging region 86. In turn, the emitted light may then pass through the central polarization filter 224, where the reflected light is then polarized in a second direction of polarization by the central polarization filter 224 that is perpendicular to the first direction of polarization associated with the polarization filter 222. In this regard, light emitted from the housing 210 may be polarized in the first direction of polarization by the peripheral polarization filter 222, be reflected back from the medical dose preparation region 86 such that the polarization of at least some of the light is changed, and be polarized in the second direction of polarization by the central polarization filter 224. The result may be reduced glare on objects placed in the medical dose preparation staging region 86. For example, especially in the case of shiny materials such as glass, light that impinges on an object in the medical dose preparation staging region 86 normal to the surface may not undergo a change in polarization. Thus, the light incident normal to the object that may result in glare does not change in polarization from the first direction. The introduction of the central polarization filter 224 with a polarization in the second direction may fully block the reflected light that is still in the first polarization direction because the light was reflected normal to the surface, thus reducing the glare the light in the first polarization direction may otherwise produce.

Figure 6:
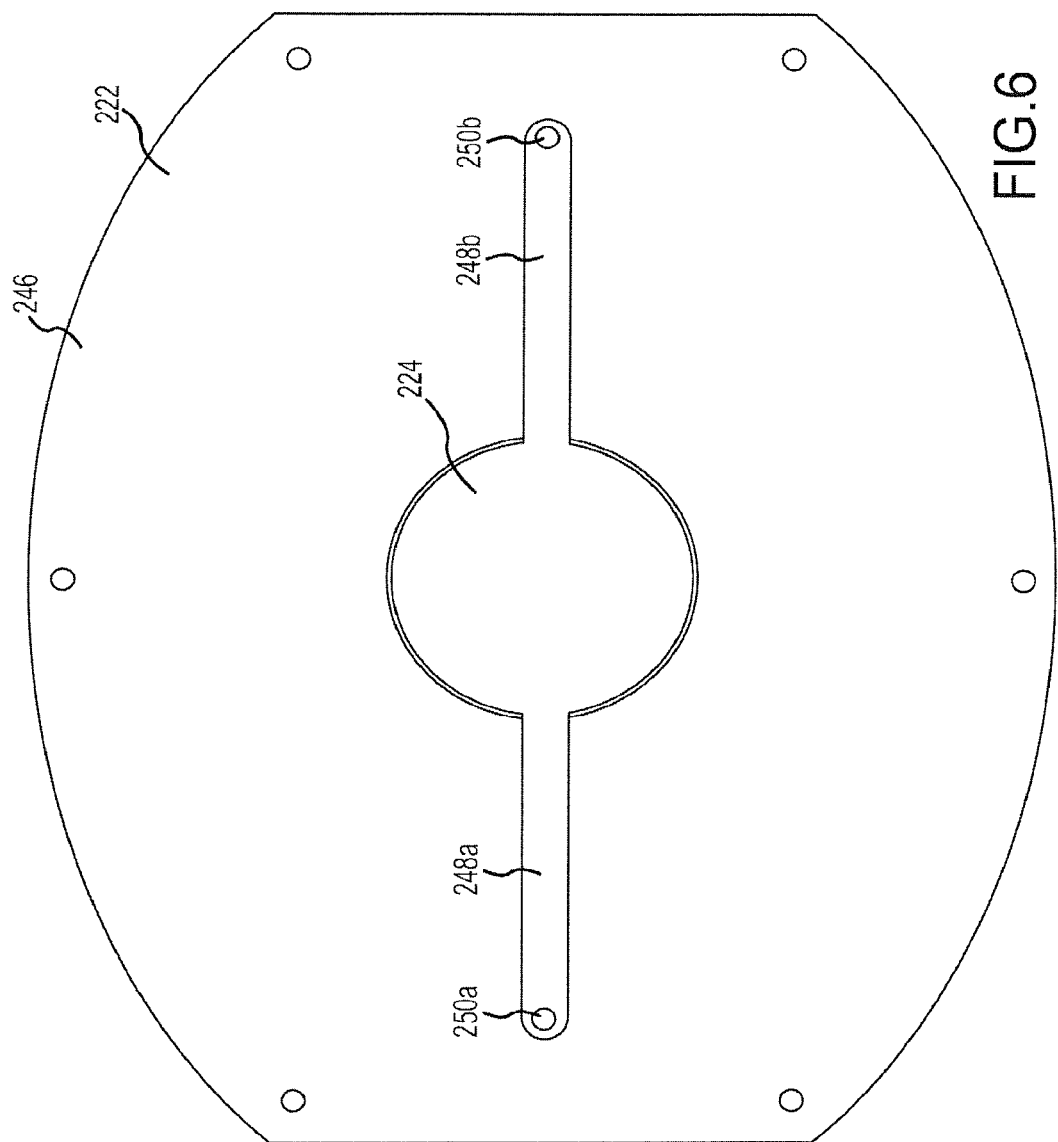
FIG. 6 depicts an embodiment of a polarization filter during production of the polarization filter.
Figure 7:
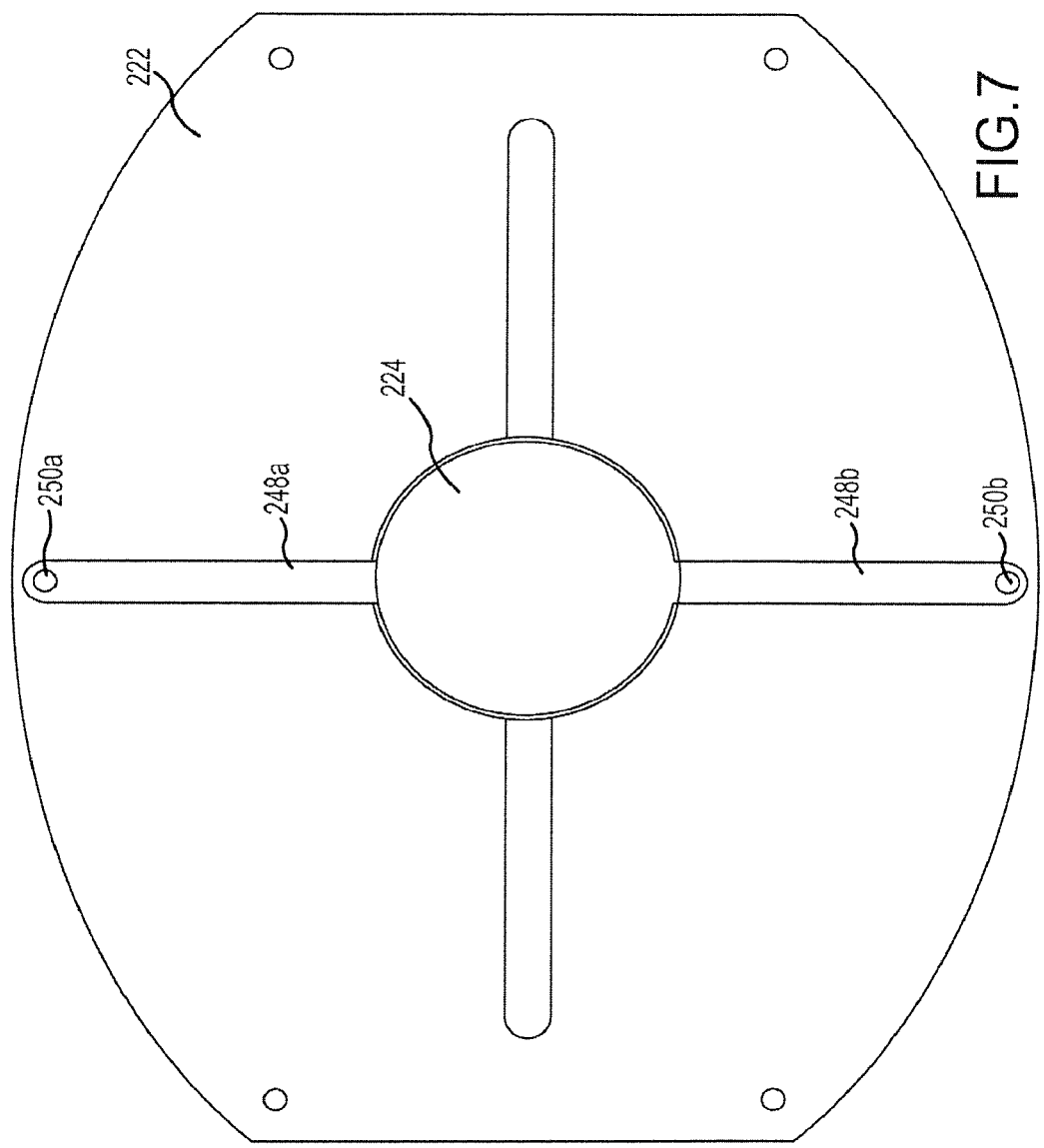
FIG. 7 depicts the embodiment of the polarization filter of FIG. 6 in a finished and aligned state.

To achieve the foregoing relative orientations of the polarization of the peripheral polarization filter 222 and the central polarization filter 224, the respective filters may be manufactured from a unitary sheet of polarized material. With respect to FIG. 6, the central polarization filter 224 may be cut from a unitary sheet of polarizing material 246 with a single polarization orientation. The central polarization filter 224 may include wings 248a and 248b, each having a mounting hole 250a and 250b, respectively. With further reference to FIG. 7, once the central polarization filter 224 has been separated from the unitary sheet of polarizing material 246, it may be rotated 90° relative to the remainder of the unitary sheet of polarizing material 246 now comprising the peripheral polarization filter 222. In this regard, the polarization directions of the central polarization filter 224 may be perpendicular to the peripheral polarization filter. Furthermore, the separation of the central polarization filter 224 from the peripheral polarization filter 222 may provide the non-overlapping relation between the central polarization filter 224 and peripheral polarization filter 222 (e.g., with the exception of the wings 248a and 248b of the central polarization filter 224). In other embodiments, completely separate portions may be provided that define the central polarization filter 224 and the peripheral polarization filter 222. As such, the polarization directions of the separate portions may be tested and aligned appropriately to achieve perpendicular relative orientations of the polarization directions.

Additionally or alternatively, other optical filters may be provided other than the polarization filters described above. For example, a diffusion filter may be provided that may provide more uniform light distribution at the medical dose preparation staging region 86. Other optical filters such as high pass, low pass, band pass, or any other appropriate optical filters may be employed to selectively control the emission of light from the light source. Additionally, light sources that emit certain wave length light may also be employed. Further still, light sources may be employed that are operable to controllably emit different wave length light (e.g., the color of the light may be controlled).

It may be appreciated in FIG. 5 that the camera 212 is contained in the enclosed volume 218. In this regard, access to the camera 212 may be limited. Accordingly, optical settings associated with the camera 212 may not be modifiable by a user by manipulation of the camera 212 directly. It has been found that often in an effort to improve image quality, an operator may adjust the optical settings of a camera 212. However, the resulting adjustments may ultimately degrade the quality of images resulting in sub-optimal focus and/or aperture settings for a variety of images to be captured using the camera 212.

Accordingly, in an embodiment, the camera 212 includes at least one fixed optical setting. For example, one or more optical settings may be fixed such that a depth of field of the camera 212 as defined by the lens 226 encompasses at least a portion of the medical dose preparation staging region 86. In an embodiment, at least a majority of the medical dose preparation staging region 86 is encompassed by a depth of field of the camera 212. In an embodiment, substantially all of the medical dose preparation staging region 86 is encompassed by a depth of field of the camera 212. The fixed optical settings of the camera 212 may comprise a focus setting, an aperture setting, a magnification, or another optical setting affecting the depth of field of the camera 212.

In another embodiment, the optical settings of the camera 212 may be adjustable (e.g., by a user). For example, a focal length, magnification, or other optical parameter of the camera 212 may be adjusted. The adjustment of the optical settings may be manually accomplished by a user manipulating a portion of the camera 212. In an application, an electronic signal may be provided to the camera 212 in order to adjust the optical settings thereof. In an embodiment, camera 212 may be continuously adjustable through a continuum of settings associated with one or more optical parameters. In another embodiment, a plurality of discrete optical parameters may be selectable. For example, the optical parameters the camera 212 may be selected from among at least two different optical parameter settings. For example, a corresponding optical parameter setting may be selected based on a selected position of the camera 212 relative to the base 90. In this regard, the camera 212 may be disposed at different distances relative to the base for different positions of the support 92 and/or for different configurations of the camera stand 200. In this regard, for the various different configurations available, discrete optical setting may be provided for each position of the imaging device 80 relative to the base 90 such that the optical parameters associated with the camera 212 results in a clear image of the medication receptacle 100 being imaged by the camera 212.

In an embodiment, the light sources 230 may be used to indicate when a medical dose preparation image has been captured. That is, as described above, a user control device 130 may be used to initiate the capture of a medical dose preparation image from a video data stream 82. In a first predetermined period after the capture of the medical dose preparation image, the intensity of at least one of the light sources 230 may be changed. The change in intensity may indicate to the user that the image has successfully been captured. In this regard, the light intensity of the light source 230 may change from a default level to a modified intensity (e.g., either more or less intense). The light source 230 may then return to the default intensity after a second predetermined period of time. In this regard, the light source 230 may "blink" or "flicker" or momentarily change from the default intensity to a modified intensity and then return to the default intensity). The variation in intensity may be readily perceived by a user to indicate the image has been captured and that the medical dose preparation staging region 86 may be cleared and, for example, prepared for the next image.

Returning to FIG. 3, the housing imaging device 80 may be supportably engaged by a support 92. The support 92 may allow for selectively positioning the support 92 in at least a first position and a second position relative to the medication preparation staging region 86. For example, the support 92 may be selectively positionable between the orientation shown in FIG. 3 (referred to herein as a first position) and that shown in FIGS. 8 and 9 (referred to herein as a second position).

In this regard, the support arm 92 may include a first portion 234 and a second portion 236. The first portion 234 may be supportably engaged with the housing 210 and the second portion 236 may be supportably engaged with the base 90. The first portion 234 may be positionably attached to the second portion 236 at a connection 238. For example, the first portion 234 may be moveably attached to the second portion 236 such that the first portion 234 may undergo relative movement with respect to the second portion 236 to move between the first position depicted in FIG. 3 and the second position depicted in FIG. 10. In this regard, the connection 238 may comprise a hinge to provide pivotal movement between the first portion 234 and the second portion 236 between the first position and the second position.

The movement of the first portion 234 relative to the second portion 236 may be dampened and/or dampenable. In this regard, connection 238 may include a dampener that dampens movement of the first portion 234 relative to the second portion 236. In one embodiment, the dampener may comprise coordinating elliptical profiles provided on each of the first portion 234 and the second portion 236 at the connection 238. The elliptical profiles may be provided as coordinating surfaces of the first portion 234 and the second portion 236. Other shaped profiles may be provided other than elliptical profiles such as, for example, a non-uniform contoured shape (e.g., profile defining one or more cam lobes).

Figure 10A:
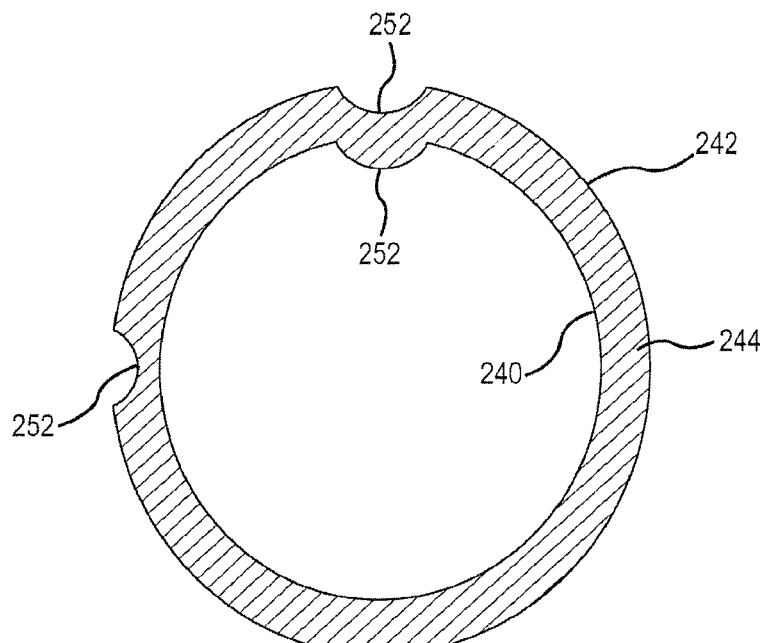
FIGS. 10A and 10B depict an embodiment of a connection between a first portion and a second portion of a support in a first position and a second position, respectively.
Figure 10B:
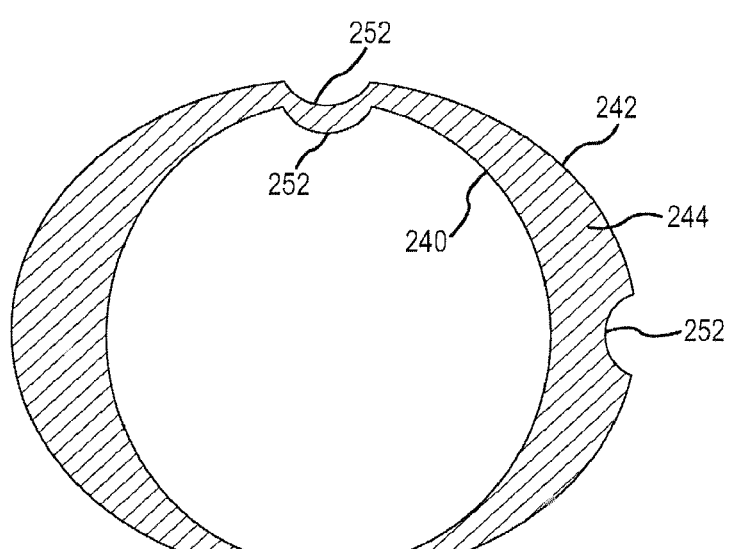
Figure 11:
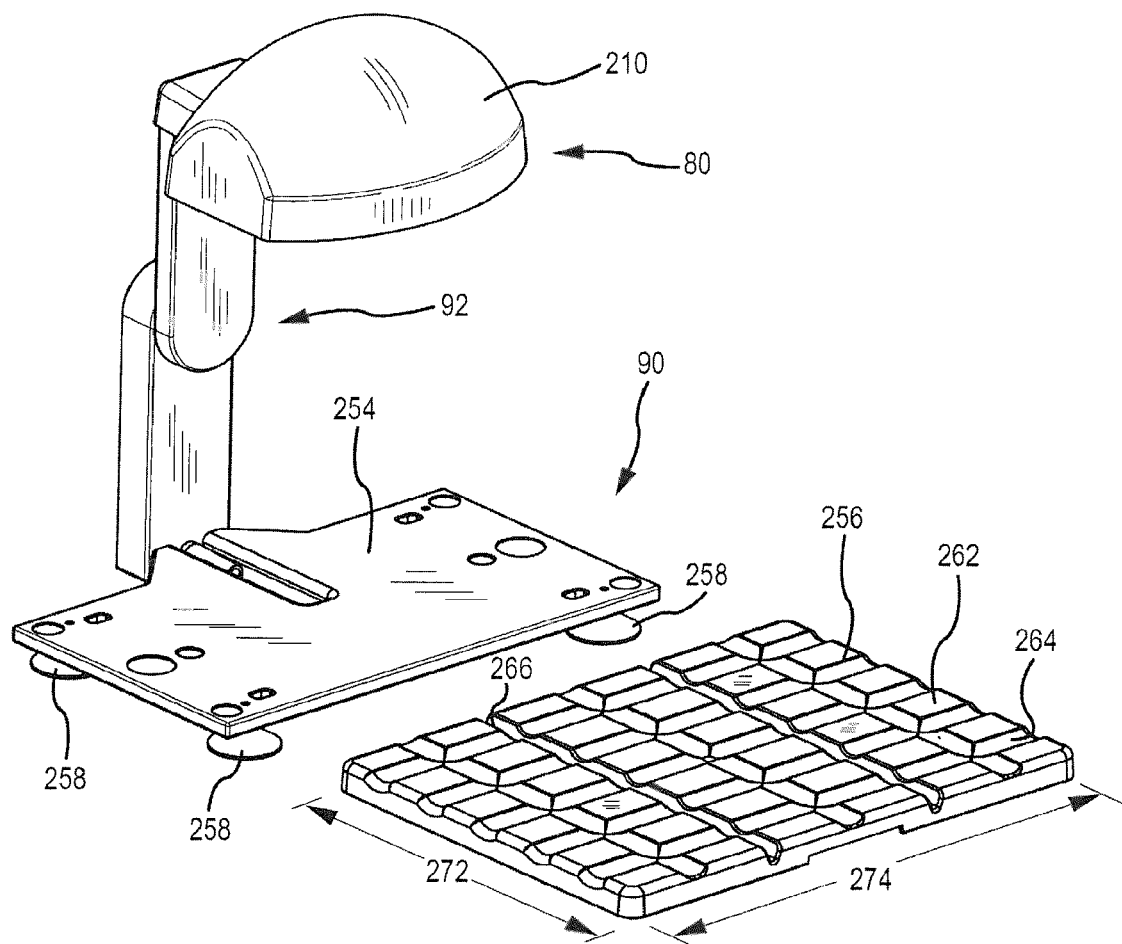
FIG. 11 is a perspective view of a base of the camera stand of FIG. 3 with a support platform in a removed position.

One embodiment illustrating the use of coordinating elliptical surfaces to achieve dampened movement between the first portion 234 and the second portion 236 is shown in FIGS. 10A and 10B. For example, a first elliptical surface 240 may be provided on the first portion 234 and a second elliptical surface 242 may be provided on the second portion 236. The elliptical surfaces 240 and 242 may be concentrically disposed and separated by a resilient material 244 (e.g., a resilient o-ring or the like). Upon pivotal movement of the first portion 234 relative to the second portion 236, the elliptical surfaces 240 and 242 may converge, resulting in compression of the resilient material 244, thus dampening movement between the first portion 234 and the second portion 236. Also, coordinating detent features 252 may be provided for registration of the first portion 234 relative to the second portion 236 at the first position 234 and the second position 236. The damping may be non-uniform through the movement of the first portion 234 and the second portion 236. For example, the damping force acting in response to movement between the first portion 234 and the second portion 236 may be less as the first portion 234 and the second portion 236 move toward the first position (shown in FIG. 3). Thus, the positioning of the first portion 234 relative to the second portion 236 may be more precise given the damping force is less near this point than at other points of travel between the first portion 234 and the second portion 236.

Figure 8:
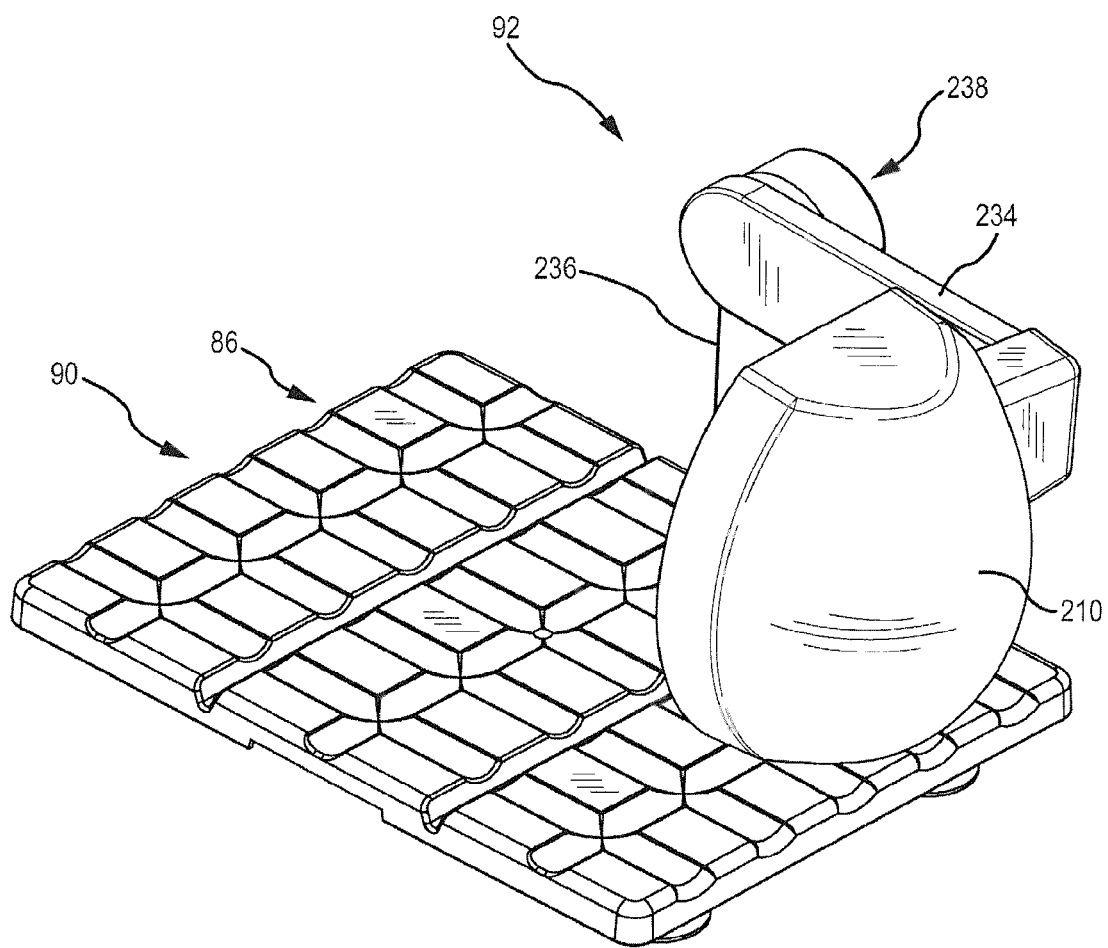
FIG. 8 is a perspective view of the embodiment of the camera stand of FIG. 3 with a support disposed in a second position.
Figure 9:
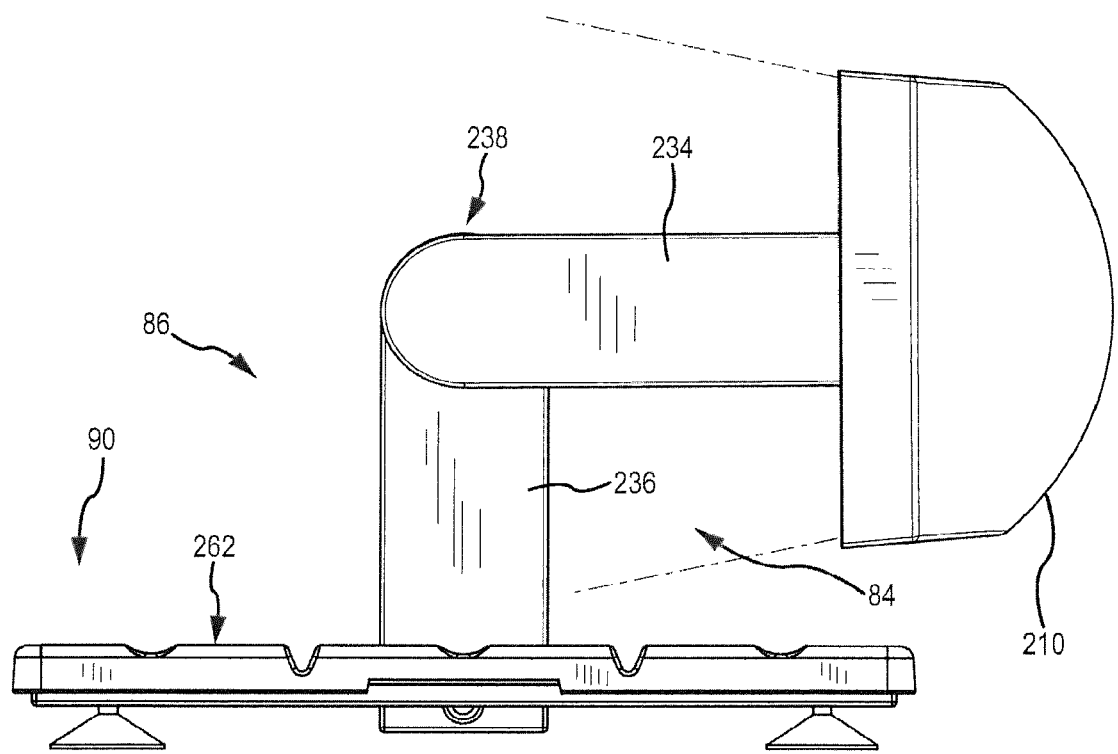
FIG. 9 is a plan view of the embodiment of the camera stand of FIG. 3 with the support disposed in the second position.

As may be appreciated in FIGS. 3 and 8-9, the first position (shown in FIG. 3) of the support 92 may dispose the imaging device 80 such that the imaging field 84 of the imaging device 80 is oriented in a manner such that the medication preparation staging region 86 is disposed between the imaging device 80 and the base 90. That is, the camera 212 may be directed at the base 90 such that the medication preparation staging region 86 defined by the base is between the camera 212 and the base 90 and in the imaging field 84 of the camera 212. In this regard, a medical dose preparation image captured by the camera 212 may include an image whose dimensions correspond to a length and width of the medication preparation staging region 86.

In the second position (shown in FIG. 10) the imaging device 80 may be oriented with respect to the base 90 such that the imaging field 84 of the imaging device 80 extends parallel to a plane defined by a support surface 262 of the base 90 that is described in greater detail below. That is, the camera 212 may be directed perpendicularly to the base 90 such that the imaging field 84 extends in a direction parallel to the support surface of the base to encompass at least a portion of the medical dose preparation staging region extending normal to the base 90.

The support 92 may also contain at least a portion of an umbilical 268 that may be operable to establish communication between the components disposed in the enclosed volume 218 (e.g., the camera 212, the light source board 228, light sources 230, etc.). In this regard, the umbilical 268 may establish electrical communication paths between the components in the enclosed volume 218 and the processor 70. In some embodiments, the umbilical 268 may include one or more bundled or consolidated cables, one or more conductive traces, a plurality of wires, or other appropriate conductors to establish electrical communication between the components in the enclosed volume 218 and the processor 70. As shown in FIG. 3, the umbilical 268 may extend from the camera 212 and/or the light source board 228 and pass into a passage 270 defined in first portion 234. The passage 270 may extend from the first portion 234 to the second portion 236. In this regard, the connector 238 may facilitate passage of the umbilical 268 therethrough. For example, the umbilical 268 may pass through the second portion 236 and emerge therefrom. The umbilical 268 may include a connector at an end opposite that in communication with the components in the enclosed volume 218 that may be used to establish electrical communication with the processor 70. For example, the connector may be a proprietary or standard connector (e.g., a USB connector or the like).

It may be noted that the umbilical 268 may provide electrical communication paths for a plurality functions. For example, signal paths and/or power communication paths may be provided in the umbilical 268. In this regard, plurality of discrete electrical communication paths may be consolidated into a single cord extending from the camera support 200. In the context of a work station 40, the minimization of wires in the work area may provide advantages, especially in the context of cleaning the workstation 40. That is, the fewer wires present in a work area (such as a laminar flow hood, isolator, or biological safety cabinet) the easier the work station 40 may be to clean.

Furthermore, in the context of, for example, a biological safety cabinet, it may be appreciated that elimination of wires or cables extending from the camera stand altogether may be particularly advantageous. For example, a biological safety cabinet may provide complete isolation from an external environment. In this regard, should a camera stand 200 include a cord, the cord may be required to pass through the wall of the biological safety cabinet. However, a minimum level of containment must also be maintained, which may be difficult or costly to achieve while facilitating passage of the cord through the cabinet wall. In this regard, it is contemplated that the camera stand 200 may be completely wireless. For example, wireless technology may be incorporated to the camera stand 200 to facilitate communication of electronic signals between the camera stand 200 and the processor 70. Examples of such wireless technology include Wi-Fi, Bluetooth, or other wireless vacation technologies. Furthermore, the camera stand 200 may be equipped with a battery to provide operational power to the camera stand 200. The battery may be removable, replaceable, and/or rechargeable to facilitate wireless operation of the camera stand 200. For example, a lithium-ion battery or other appropriate type of battery may be provided in the camera stand 200. The battery and provided any portion of the camera stand 200 without limitation including for example, the base 90, the support 92, and/or the enclosed volume 218.

Figure 15:
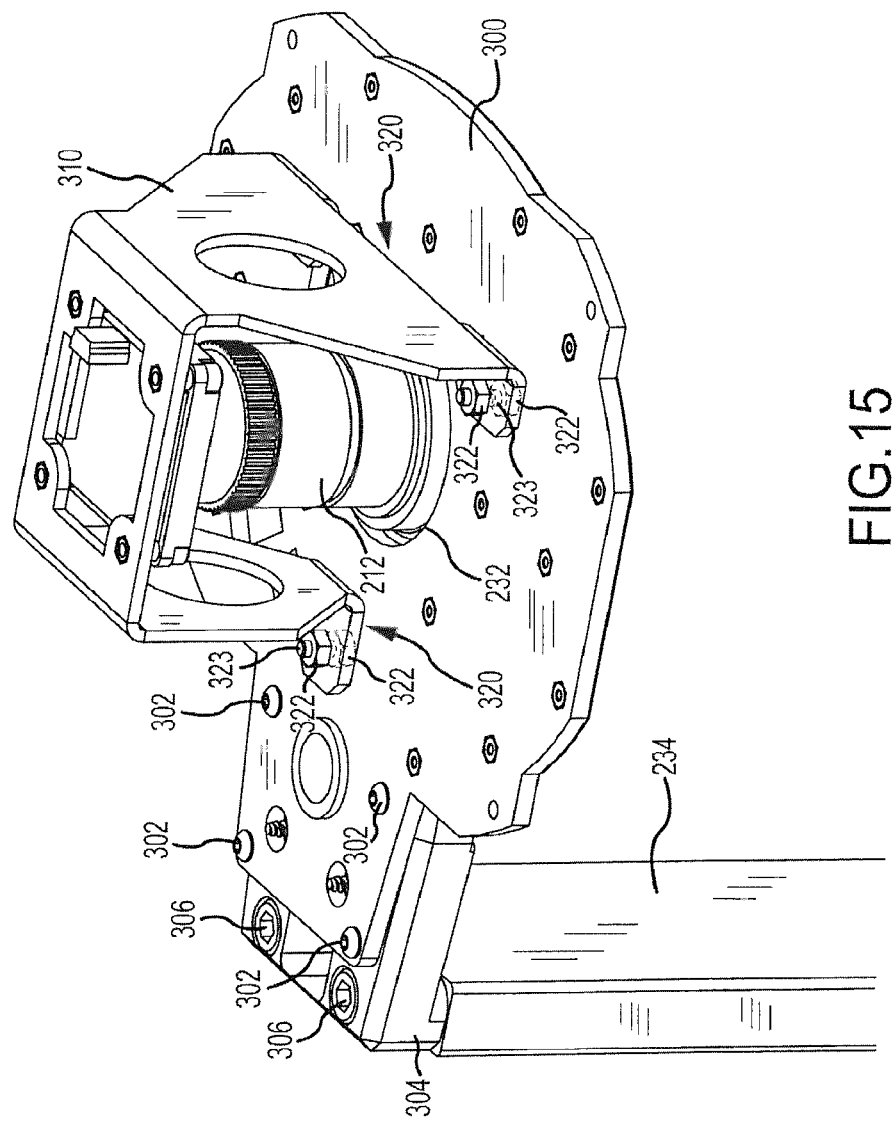
FIG. 15 is a perspective view illustrating an embodiment of an attachment of an imaging device to a support.

With further reference to FIG. 15, a mechanism for attaching the camera 212 to the first portion 234 of the support 92 is shown. It may be appreciated that the camera 212 may be subject to an image tolerance associated with the alignment of the camera 212 to the base 90. Misalignment between the camera 212 in the base 90 may result in image distortion such as keystoning or the like. In this regard, the image tolerance associated with the alignment between the camera 212 of the base 90 may be important to obtain quality medical dose preparation images using the camera 212. However, manufacturing considerations associated with providing connection tolerances between various pieces comprising the camera stand 200 may make it difficult to achieve the image tolerance to provide accurate camera alignment during manufacturing. That is, the camera 212 may include an imaging tolerance that is more restrictive than the connection tolerances provided in the attachment of the camera 212 to the camera stand 200. For example, connection tolerances may be introduced, inter alia, at the interface between the base and second portion 236 of the support 92, the first portion 234 and the second portion 236, the attachment of a mounting plate 300 and the first portion 234, and the interface to the camera 212 and associated mounting structure. Furthermore, it may be appreciated that the tolerances associated with each of these interfaces may present a tolerance stack up problem that may result in misalignment of the camera 212 with respect to the base 90.

Accordingly, as depicted in FIG. 15, a mounting plate 300 may be secured by way of fasteners 302 to an attachment member 304. The attachment member 304 may be secured to the first portion 234 by way of fasteners 306. A mounting structure 310 may be secured to the mounting plate 300. The camera 212 may be mounted to the mounting structure 310. The interface between the mounting structure 310 and the mounting plate 300 may define a gimbal 320. The gimbal 320 may allow for adjustable movement of the camera 212 in at least a first (and potentially two, three, or more) directions. The gimbal 320 may include one or more jack nuts 322 that may allow the mounting structure 310 to be adjustably positioned relative to the mounting plate 300. For example, the jack nuts 322 may include coordinating nut pairs provided on a threaded stud 323 such that the attachment of the mounting structure 310 relative to the mounting plate 300 may be adjusted up and down along the threaded studs 323 (e.g., at three locations as shown in FIG. 15 to control movement of the camera 212 in at least two directions) Accordingly, the camera 212 may be adjusted or aimed by manipulating the jack nuts 322 to modify the orientation of the camera 212 once secured to the mounting structure 310.

In this regard, it may be appreciated that once the attachment member 304 is secured to the first portion 234, the mounting plate 300 is secured to the attachment member 304, the mounting structure 310 is secured to the mounting plate 300, and the camera 212 secured to the mounting structure 310, the alignment of the camera 212 may be non-perpendicular to the base 90 (i.e., the imaging tolerance may not be achieved). In this regard, the jack nuts 322 may be manipulated so as to align the camera 212 to be substantially perpendicular to the base 90 such that any image distortion such as keystoning may be eliminated from the resultant image obtained by camera 212. In other words, the imaging tolerance may be achieved via adjustment of the gimbal 320. As such, the amount of adjustment provided by the gimbal 320 may at least correspond to the difference between the connection tolerance and the imaging tolerance associated with the alignment of the camera 212 to the base 90.

It may be appreciated that the mounting plate 300 and/or mounting structure 310 may be fabricated from sheet material. In this regard, the manufacturer of these components may be provided at significant lower cost than other manufacturing techniques that may be employed when tolerances are required to be relatively high. In this regard, the use of the gimbal 320 provide adjustability of the alignment of the camera 212 once secured to a mounting structure may allow for manufacturing techniques that are less costly to be employed when manufacturing the camera stand 200.

While not shown in FIG. 15, it may be appreciated that the housing 210 and/or transparent shield 216 may be secured to the mounting plate 300 and/or mounting member 304. In this regard, the housing 210 and/or transparent shield 216 may be secured relative to the mounting plate 300 and/or mounting member 304 to define the enclosed area 218.

Figure 12:
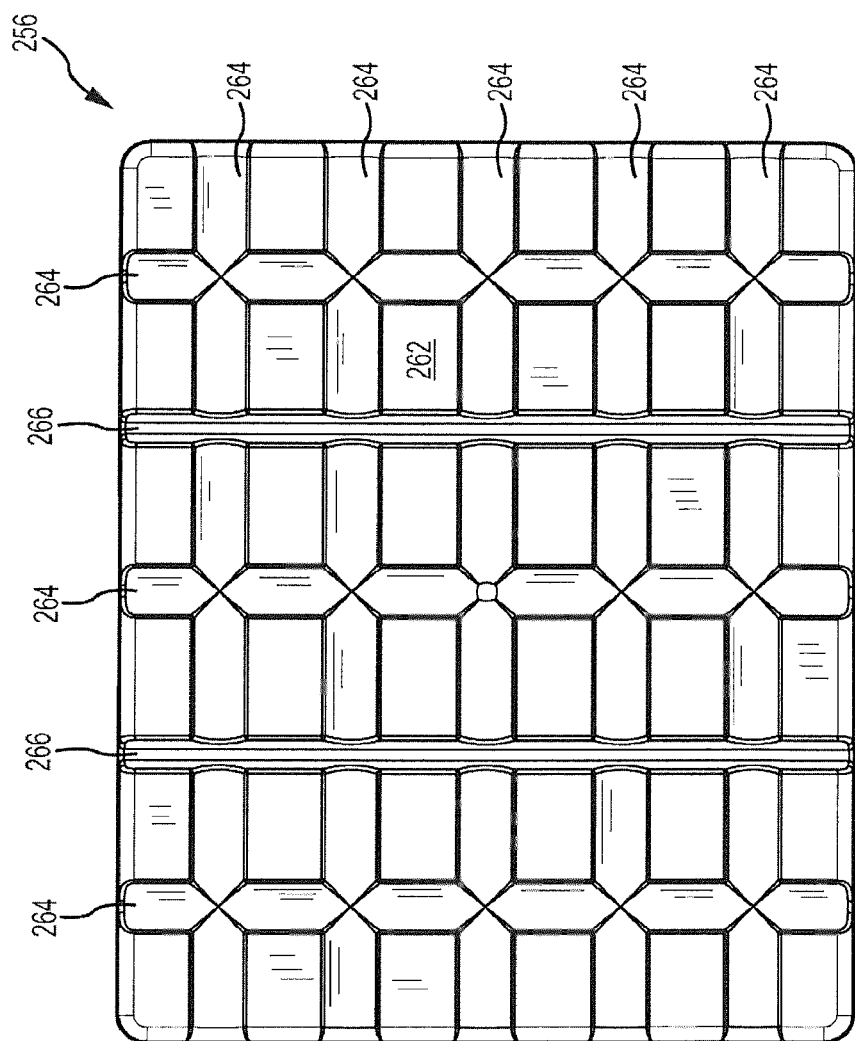
FIG. 12 is a top view of an embodiment of a support surface of a work station.

With further reference to FIG. 12, the base 90 of the camera stand 200 may include a platform base 254 and a support platform 256 that is removably disposable relative to the platform base 254. In this regard, the support platform 256 may be removed, for example, to undergo cleaning or the like. The platform base 254 may include one or more feet 258 that may engage a surface on which the platform base 254 is disposed. For example, the platform-based 254 may include one or more suction cup bases 276 may be used to secure the base 90 and in turn the camera stand 200 to the surface. The suction cup bases 276 may provide secure attachment to the surface to provide stable operation of the camera stand 200. That is, suction cup bases 276 may at least partially isolate vibrations to improve the image obtained by the camera 212 when capturing a medical dose preparation image as described above. The support platform 256 may be constructed of a UV resistant material.

The support platform 256 may have a length 272 and a width 274. In this regard, when the support platform 256 is disposed on the platform base 254, the length 272 and width 274 may define dimensions of the base 90. The length 272 and the width 274 may also correspond to a medical preparation staging region 86 at least partially defined by the support platform 256.

Additionally, with reference to FIG. 4, it may be appreciated that the peripheral region of the opening 214 of the housing 210 may extend in a first direction corresponding to the length 274 of the support platform 90. The peripheral region may extend in the first direction corresponding to the length 274 of the base 90 both when the support 92 is in the first position shown in FIG. 3 and the second position shown in FIGS. 8-9. The peripheral region may extend in a second direction corresponding to the width 274 of the support platform 256 when the support 92 is in the first position. When the support is in the second position (as best seen in FIG. 9), the peripheral region may extend in a direction corresponding to a height of the medical dose preparation region 86 extending normal to the support platform 256.

The platform base 254 may include a scale such that an item disposed on the support platform 256 when disposed on the platform base 254 may be weighed. For example, the weight measured by the scale may be captured substantially simultaneously as the capture of a medical dose preparation image by the imaging device 80. Accordingly, the weight obtained by the scale may be appended to the dose order metadata. In an embodiment, the processor 70 at the processor or a remote processor with access to the metadata may perform a gravimetric analysis using a weight measured by the scale to, for example, compare the measured weight to an anticipated weight for the medical dose. The scale may comprise load cells disposed in the platform base 254 (e.g., at each foot 258 of the platform base 258 or adjacent to where the support platform 256 is supported.

In this regard, the anticipated weight for the medical dose may be contained in the metadata to assist in a gravimetric analysis of the medication receptacle 100. The processor 70 at the work station 40 may associatively store the anticipated weight and the measured weight. Furthermore, the processor may be operable to compare the measured weigh to the anticipated weight. In an embodiment, a deviation of the actual weight from the anticipated weight may be calculated and if the deviation exceeds a threshold, an alarm may be provided to the user.

The support platform 256 may at least partially define the medication preparation staging region 86. For example, the medication preparation staging region 86 may encompass a volume extending in a direction normal to a support surface 262 of the support platform 254. As such, a receptacle supportably engaged by the support platform 254 may be encompassed by the medication preparation staging region 86 such that the receptacle is disposed in the imaging field of the imaging device 80.

Figure 13:
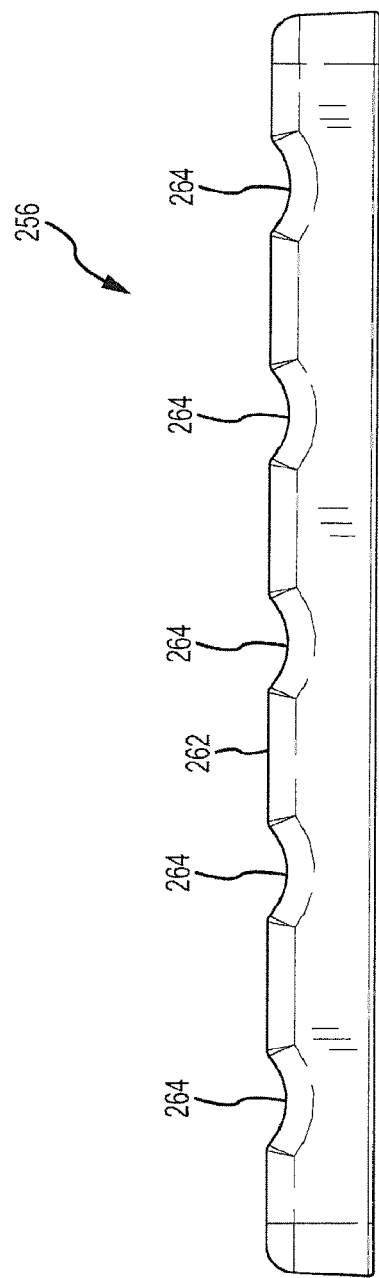
FIGS. 13 and 14 are front and side views, respectively, of the support surface of FIG. 12.
Figure 14:
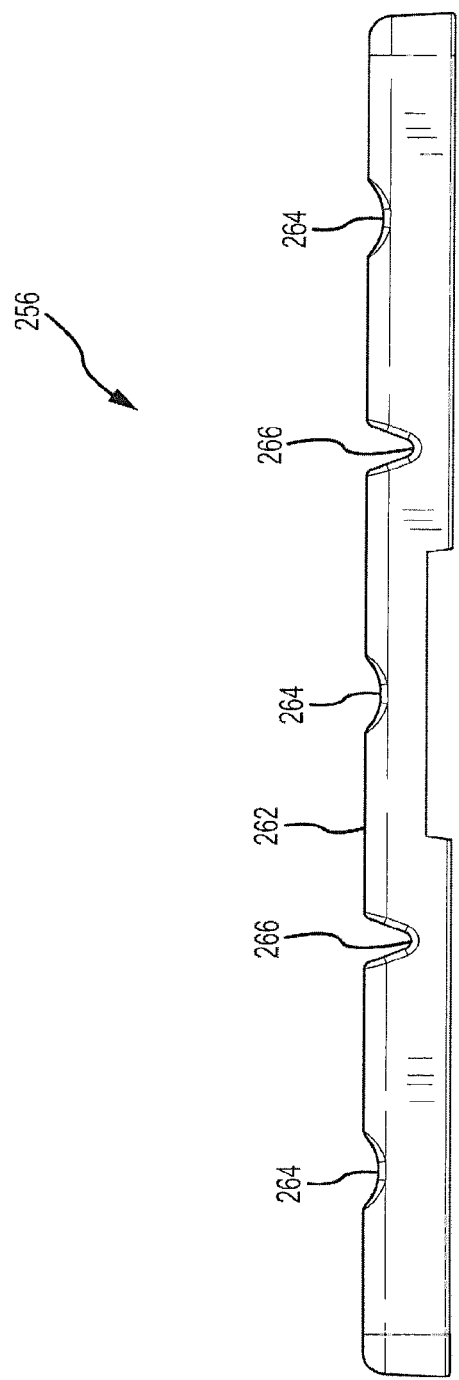

The support platform 254 may also include one of more medication receptacle engagement feature that may engage a medical receptacle that is supportably disposed with respect to the support platform 254. For example, the medication receptacle engagement features may include at least one groove 264 and at least one channel 266. With further reference to FIGS. 13-15, the features described comprising the support platform 254 may be further appreciated. The grooves 264 may extend from the support surface 262 a first depth. The channels 266 may extend from the support surface 262 a second depth. The first depth may be less than the second depth. That is, the grooves 264 may be shallower with respect to a depth extending from the support surface 262 than the channels 266. The engagement features described herein may extend across substantially all of the support platform 254, and in turn, the medication preparation staging region 86 at least partially defined by the support platform 254. In an embodiment, at least a portion of the grooves 264 extend in a direction different than at least a portion of the channels 266. For example, at least a portion of the grooves 264 may extend perpendicularly to the channels 266. In addition, at least a portion of the grooves 264 may extend in a direction corresponding to the channels 266.

The grooves 264 may have a first radius of curvature in a direction corresponding to the first depth from which the grooves 264 extend from the support surface 262. In this regard, the grooves 264 may have a generally concave profile. For example, a concave surface profile may be defined along the groove 264. Similarly the channel 266 may include a second radius of curvature in a direction corresponding with the second depth. In this regard, the channels 266 may also have a generally concave profile (e.g., a concave surface profile). The first radius of curvature may be larger than the second radius of curvature such that the grooves 264 include a shallower profile versus a steeper profile of the channels 266.

In an embodiment, the grooves 264 may be adapted to engage a first portion of a medication receptacle. For example, the concave surface profile of the grooves 264 may correspond with the circumference of the barrel of a syringe. In this regard, the syringe barrel may be received in the grooves 264 such that movement of the syringe barrel corresponding to rolling of the syringe may be restricted when disposed on the support platform 256 and engaged by a groove 264. In a similar regard, the channels 266 may be adapted to engage a second portion of a medication receptacle. For example, the concave surface profile of the channels 266 may correspond with finger rest of a syringe. Additionally or alternatively, the concave surface profile of the channels 266 may correspond with a plunger end. In this regard, when the barrel of a syringe is disposed in a groove 264, the finger rest and/or plunger end of the syringe may be engaged by the channel 266 that may restrict motion of the syringe along the length of the groove 264. As such, the syringe may be constrained in at least two degrees of freedom to reduce the potential the syringe mistakenly moves (e.g., slides, is disrupted, or otherwise moved) from the support platform 256. It may also be appreciated that the concave surface profile of the grooves 264 and/or the channels 266 may be operable to retain a cylindrical body (e.g., a vial, bottle, or other cylindrical container) to prevent rolling movement thereof.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A work station for use in a system for medical dose preparation management, the work station comprising:
   a base and a medication preparation staging region disposed relative thereto;
   an imaging device having an imaging field encompassing at least a portion of the medication preparation staging region, the imaging device being located at least partially within a housing;
   at least one light source disposed in the housing, wherein the at least one light source is operable to emit light from the housing in a direction toward the medication preparation staging region;
   a support member extending between the base and the housing for supportably disposing the imaging device relative to the base; and
   a user control device for receiving a user input to initiate capture of a medical dose preparation image from a video data stream output by the imaging device, wherein an intensity of the at least one light source is automatically modified from a default intensity of light emitted to a modified intensity of light emitted at a first predetermined period after the capture of the medical dose preparation image.

2. The work station of claim 1, wherein the at least one light source is adapted to indicate the capture of a medical dose preparation image to a user.

3. The work station of claim 2, wherein the at least one light source is adapted to provide the alert.

4. The work station of claim 1, wherein an alert is provided to a user after the capture of the medical dose preparation image.

5. The work station of claim 1, wherein the at least one light source is automatically returned from the modified intensity of light to the default intensity of light at a second predetermined period after the first predetermined period.

6. A work station for use in a system for medical dose preparation management, the work station comprising:
   a base having a length and a width;
   a medication preparation station region disposed relative to the base;
   an imaging device disposed in a housing and having an imaging field encompassing at least a portion of the medication preparation staging region;
   a light source disposed in the housing, wherein the light source is operable to emit light from the housing in a direction toward the medication preparation staging region;
   a support member extending between the base and the housing for supportably disposing the imaging device relative to the base, wherein the support member is selectively positionable in at least a first position and a second position relative to the medication preparation staging region; and
   a user control device for receiving a user input to initiate capture of a medical dose preparation image, wherein an intensity of the at least one light source is automatically modified from a default intensity of light emitted to a modified intensity of light emitted at a first predetermined period after the capture of the medical dose preparation image.

7. The work station of claim 6, wherein the support member is moveable between the first position and the second position.

8. The work station of claim 6, wherein the support member is selectively positionable in a plurality of different positions relative to the medication preparation staging region.

9. The work station of claim 6, wherein the support member comprises a first portion attached to the base and a second portion attached to the housing, wherein the second portion is moveable relative to the first portion between the first position and the second position.

10. The work station of claim 9, wherein the first portion is hingedly connected to the second portion.

11. The work station of claim 9, wherein the first portion and the second portion are pivotally disposable between the first position and the second position.

12. The work station of claim 6, wherein the base comprises a support surface extending along the length and the width.

13. The work station of claim 6, wherein the movement between the first position and the second position is dampened.

14. A work station for use in a system for medical dose preparation management, the work station comprising:

a base;

a support platform removably disposable relative to the base, the support platform defining a medication preparation staging region;

a support surface of the support platform defining a plurality of medication receptacle engagement features;

an imaging device supportably engageable relative to the base and having an imaging field encompassing at least a portion of the medication preparation staging region;

a light source; and a user control device for receiving a user input to initiate capture of a medical dose preparation image, wherein an intensity of the at least one light source is automatically modified from a default intensity of light emitted to a modified intensity of light emitted at a first predetermined period after the capture of the medical dose preparation image.

15. The work station of claim 14, wherein the light source is adapted to indicate the capture of a medical dose preparation image to a user.

16. The work station of claim 14, wherein an alert is provided to a user after the capture of the medical dose preparation image.

17. The work station of claim 16, wherein the light source is adapted to provide the alert.

* * * * *